United States Patent [19]
Morishita et al.

[11] Patent Number: 5,840,518
[45] Date of Patent: Nov. 24, 1998

[54] DNA FRAGMENT, VECTOR CONTAINING THE DNA FRAGMENT, TRANSFORMANT TRANSFORMED WITH THE VECTOR AND PROCESS FOR PRODUCING PROTEIN USING THE VECTOR

[75] Inventors: Hideaki Morishita; Toshinori Kanamori; Masahiro Nobuhara, all of Tokyo, Japan

[73] Assignee: Mochida Pharmaceutical Co. Ltd., Tokyo, Japan

[21] Appl. No.: 235,515

[22] Filed: Apr. 29, 1994

[30] Foreign Application Priority Data

May 1, 1993 [JP] Japan ................................ 5-128528

[51] Int. Cl.$^6$ ........................ C12N 15/00; C12N 15/11; C12N 15/70; C12P 21/02
[52] U.S. Cl. ............... 435/69.1; 435/252.3; 435/252.33; 435/252.31; 435/254.2; 435/320.1; 530/23.4
[58] Field of Search .............................. 435/69.1, 172.3, 435/320.1, 252.3–252.35, 254.2; 536/23.4, 23.7

[56] References Cited

FOREIGN PATENT DOCUMENTS

| | | |
|---|---|---|
| 0 255011 | 2/1988 | European Pat. Off. . |
| 0 401508 | 12/1990 | European Pat. Off. . |
| 0 543240 | 5/1993 | European Pat. Off. . |

OTHER PUBLICATIONS

Watanabe et al, Abstracts of Papers, Annual Meeting of Agric. Chem. Soc., p. 425, Japan (1984).
Shine et al, Proc. Nat. Acad. Sci. USA, vol. 71, No. 4, pp. 1342–1346 (1974).
Rao et al, Gene, vol. 3, pp. 247–263 (1978).
De Boer et al, Proc. Natl. Acad. Sci. USA, vol. 80, pp. 21–25 (1983).
Charette et al, Proc. Natl. Acad. Sci. USA, vol. 78, No. 8, pp. 4728–4732 (1981).
Chung et al, Proc. Natl. Acad. Sci. USA, vol. 78, No. 8, pp. 4931–4935 (1981).
Nakamura et al, The EMBO Journal, vol. 1, No. 6, pp. 771–775 (1982).
Kaumeyer et al, Nucleic Acids Res. 14: 7839 (1986).

*Primary Examiner*—James Martinell
*Attorney, Agent, or Firm*—Birch, Stewart, Kolasch & Birch,L LP

[57] ABSTRACT

DNA fragments having a nucleotide sequence represented by x and vectors containing the DNA fragment, wherein the nucleotide sequence x encodes an amino acid sequence represented by any one of the following formulae 1 to 8:
formula 1 AVLPQEEEGSG,
formula 2 AVLPQEEEGSGGGQLVTEVTKKEDSG,
formula 3 AVLDQEEEGSG,
formula 4 AVLPQEEEGDG,
formula 5 AVLPQEEEGSGD,
formula 6 AVLPQEEEGSGDD,
formula 7 AVLPQEEEGSGDDD, and
formula 8 ADDPQEEEGSG.

Expression of a protein of interest and its secretion from host cells into the extracellular milieu can be increased by expressing or secreting the protein of interest in the form of a fusion protein with a specified polypeptide encoded by the DNA fragment of the present invention using the vector of the present invention, by means of recombinant DNA techniques in which the inventive DNA fragment is used.

21 Claims, 14 Drawing Sheets

```
                S1
AATTCAAAAA AGGGTATAAA ATAAAATGAA ACAAAGTACT ATTGCACTGG CACTCTTACC
    GTTTTT TCCCATATTT TATTTTACTT TGTTTCATGA TAACGTGACC GTGAGAATGG
                                 S3
         S2
GTTA CTGT TT ACCCCTGTGA CAAAGGCCGC TGTGCTACCG CAAGAAGAAG AAGGCTCGGG
CAAT GACA AA TGGGGACACT GTTTCCGGCG ACACGATGGC GTTCTTCTTC TTCCGAGCCC
                                 S4
A
TTCGA
```

```
1          11         21         31         41         51
AGCTTAAAAA AGGGTATAAA ATAAAATGAA ACAAAGTACT ATTGCACTGG CACTCTTACC
    ATTTTT TCCCATATTT TATTTTACTT TGTTTCATGA TAACGTGACC GTGAGAATGG 61         71         81         91         101        111
GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC 121        131
AATGGACTCC CTAGGTCG
TTACCTGAGG GATCCAGC
```

FIG. 5

```
          10           20          30          40          50          60
5'-AAGCTT AAAAAAGGGTATAAAATAAA ATG AAA CAA AGT ACT ATT GCA CTG GCA CTC
   HindIII                    Met Lys Gln Ser Thr Ile Ala Leu Ala Leu TTA CCG TTA CTG TTT ACC CCT GTG ACA AAG GCC GCT GTG CTA CCG
       Leu Pro Leu Leu Phe Thr Pro Val Thr Lys Ala Ala Val Leu Pro CAA GAA GAA GAA GGC TCG GGA ATG GAC TCC CTA GGT CGC GAG GCC
       Gln Glu Glu Glu Gly Ser Gly Met Asp Ser Leu Gly Arg Glu Ala
                                       1               5

AAA TGT TAC AAT GAA CTT AAT GGA TGC ACC AAG ATA TAT GAC CCT
       Lys Cys Tyr Asn Glu Leu Asn Gly Cys Thr Lys Ile Tyr Asp Pro
                    10              15                      20

GTC TGT GGG ACT GAT GGA AAT ACT TAT CCC AAT GAA TGC GTG TTA
       Val Cys Gly Thr Asp Gly Asn Thr Tyr Pro Asn Glu Cys Val Leu
                    25              30                      35

TGT TTT GAA AAT CGG AAA CGC CAG ACA TCG ATC CTC ATT CAA AAA
       Cys Phe Glu Asn Arg Lys Arg Gln Thr Ser Ile Leu Ile Gln Lys
                        40              45                      50

TCT GGG CCT TGC TGA GGATCC
       Ser Gly Pro Cys ... BamHI
```

Hind III PRIMER   5' ACGCAAGTTCACGTAAAAAGC 3'

AN 6 8 PRIMER

5'   CTATTGG TAG ATT ACA GGC CGC GGC CTT TGT CAC AGG GGT   3' pBR BamHI PRIMER   5' ACGATGCGTTCCGGCGTAGAG 3'

FIG. 10

```
AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC

TATGGCCGCC TGTAATCTAC CAATAGTCCG GGGCC
ATACCGGCGG ACATTAGATG GTTATCAGGC C
```

FIG. 11

HindIII PRIMER
5'-ACGCAAGTTCACGTAAAAAGC-3'
```
ACGCAAGTTCACGTAAAAAGCTTAAAAAAGGGTATAAAATAAA ATG AAA CAA AGT ACT
              HindIII                          Met Lys Gln Ser Thr
```

```
ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys
```

```
GCC GCT GTG CTA CCG CAA GAA GAA GAA GGC TCG GGT ATG GCC GCC
Ala Ala Val Leu Pro Gln Glu Glu Glu Gly Ser Gly Met Ala Ala
                                                          1
```

```
TGT AAT CTA CCA ATA GTC CGG GGC CCC TGC CGA GCC TTC ATC CAG
Cys Asn Leu Pro Ile Val Arg Gly Pro Cys Arg Ala Phe Ile Gln
          5               10                      15
```

```
CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
          20              25                      30
```

```
TAC GGG GGC TGC CAG GGC AAC GGG AAC AAG TTC TAC TCA GAG AAG
Tyr Gly Gly Cys Gln Gly Asn Gly Asn Lys Phe Tyr Ser Glu Lys
          35              40                      45
```

```
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
          50              55                      60
```

```
                                        BamHI
CTG CTG CGC TTC TCC AAC TGA CAACTGGATCCTCTACGCCGGAACGCATCGT
Leu Leu Arg Phe Ser Asn ...       3'- GAGATGCGGCCTTGCGTAGCA-5'
          65          68          pBRBamHI PRIMER
```

FIG. 12

AGCTTAAAAA AGGGTATAAA ATAAAATGAA ACAAAGTACT ATTGCACTGG CACTCTTACC
     ATTTTT TCCCATATTT TATTTTACTT TGTTTCATGA TAACGTGACC GTGAGAATGG

GTTACTGTTT ACCCCTGTGA CAAAGGCCGC TGTGCTACCC CAAGAAGAGG AAGGATCAGG
CAATGACAAA TGGGGACACT GTTTCCGGCG ACACGATGGG GTTCTTCTCC TTCCTAGTCC

GGGTGGGCAA CTGGTAACTG AAGTCACCAA GAAAGAAGAC TCGGGTATGG CCGCCTGTAA
CCCACCCGTT GACCATTGAC TTCAGTGGTT CTTTCTTCTG AGCCCATACC GGCGGACATT

TCTACCAATA GTCCGGGGCC
AGATGGTTAT CAGGCC

FIG. 13

AGCTTAAAAA AGGGTATAAA ATAAAATGAA ACAAAGTACT ATTGCACTGG CACTCTTACC
     ATTTTT TCCCATATTT TATTTTACTT TGTTTCATGA TAACGTGACC GTGAGAATGG

GTTACTGTTT ACCCCTGTGA CAAAGGCCGC TGTGCTAGAT CAAGAAGAAG AAGGCTCGGG
CAATGACAAA TGGGGACACT GTTTCCGGCG ACACGATCTA GTTCTTCTTC TTCCGAGCCC

TATGGCCGCC TGTAATCTAC CAATAGTCCG GGGCC
ATACCGGCGG ACATTAGATG GTTATCAGGC C

FIG. 14

AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCGATGG
CAATGACAAA TGGGGACACT GTTTCCGGCG ACACGATGGC GTTCTTCTTC TTCCGCTACC

TATGGCCGCC TGTAATCTAC CAATAGTCCG GGGCC
ATACCGGCGG ACATTAGATG GTTATCAGGC C

FIG. 15

AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC

TGATATGGCC GCCTGTAATC TACCAATAGT CCGGGGCC
ACTATACCGG CGGACATTAG ATGGTTATCA GGCC

FIG. 16

AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC

TGATGATATG GCCGCCTGTA ATCTACCAAT AGTCCGGGGC C
ACTACTATAC CGGCGGACAT TAGATGGTTA TCAGGCC

FIG. 17

AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC

TGATGATGAT ATGGCCGCCT GTAATCTACC AATAGTCCGG GGCC
ACTACTACTA TACCGGCGGA CATTAGATGG TTATCAGGCC

FIG. 18

AGCTTAAAAA AGGGTATAAA ATAAAATGAA ACAAAGTACT ATTGCACTGG CACTCTTACC
   ATTTTT TCCCATATTT TATTTTACTT TGTTTCATGA TAACGTGACC GTGAGAATGG

GTTACTGTTT ACCCCTGTGA CAAAGGCCGC TGACGACCCG CAAGAAGAAG AAGGCTCGGG
CAATGACAAA TGGGGACACT GTTTCCGGCG ACTGCTGGGC GTTCTTCTTC TTCCGAGCCC

TATGGCCGCC TGTAATCTAC CAATAGTCCG GGGCC
ATACCGGCGG ACATTAGATG GTTATCAGGC C

FIG. 20

Y 4 6 D PRIMER    5'  GGG AAC AAG TTC GAC TCA GAG AAG G   3'

FIG. 21

Q 1 9 K PRIMER    5'  C AAA TGC CCA GAG CTT GAT GAA GGC TCG GCA 3'

HindIII PRIMER
5'-ACGCAAGTTCACGTAAAAAGC-3'
```
  ACGCAAGTTCACGTAAAAAGCTTAAAAAAGGGTATAAAATAAA ATG AAA CAA AGT ACT
                HindIII                       Met Lys Gln Ser Thr ATT GCA CTG GCA CTC TTA CCG TTA CTG TTT ACC CCT GTG ACA AAG
        Ile Ala Leu Ala Leu Leu Pro Leu Leu Phe Thr Pro Val Thr Lys GCC GCT GTG CTA CCG CAA GAA GAA GAA GGC TCG GGT ATG GCC GCC
            Ala Ala Val Leu Pro Gln Glu Glu Glu Gly Ser Gly Met Ala Ala
                                                                    1

TGT AAT CTA CCA ATA GTC CGG GGC CCC TGC CGA GCC TTC ATC AAG
            Cys Asn Leu Pro Ile Val Arg Gly Pro Cys Arg Ala Phe Ile Lys
                                             3'-ACG GCT CGG AAG TAG TTC
                                                              Q19K PRIMER
                    5              10                   15

CTC TGG GCA TTT GAT GCT GTC AAG GGG AAG TGC GTC CTC TTC CCC
            Leu Trp Ala Phe Asp Ala Val Lys Gly Lys Cys Val Leu Phe Pro
            GAG ACC CGT-5'
                    20              25                   30

Y46D PRIMER
                                 5'- GGG AAC AAG TTC GAC TCA GAG AAG
            TAC GGG GGC TGC CAG GGC AAC GGG AAC AAG TTC GAC TCA GAG AAG
            Tyr Gly Gly Cys Gln Gly Asn Gly Asn Lys Phe Asp Ser Glu Lys
                        35              40                   45

G-3'
            GAG TGC AGA GAG TAC TGC GGT GTC CCT GGT GAT GGT GAT GAG GAG
            Glu Cys Arg Glu Tyr Cys Gly Val Pro Gly Asp Gly Asp Glu Glu
                        50              55                   60

BamHI
            CTG CTG CGC TTC TCC AAC TGA CAACTGGATCCTCTACGCCGGAACGCATCGT
            Leu Leu Arg Phe Ser Asn ...       3'- GAGATGCGGCCTTGCGTAGCA-5'
             65            68                         pBRBamHI PRIMER
```

FIG. 23

R 1 1 S PRIMER    5' TCG GCA GGG GCC GCT GAC TAT TGG TAG  3'

FIG. 24

```
       HindIII primer
5'-ACGCAAGTTCACGTAAAAAGC-3'
   ACGCAAGTTCACGTAAAAAGCTTAAAAAAGGGTATAAAATAAA ATG AAA CAA AGT ACT
                   HindIII                     Met Lys Gln Ser Thr ATT GCA CTG GCA CTC TTA CCG TTA CTG TTT ACC CCT GTG ACA AAG
   Ile Ala Leu Ala Leu Leu Pro Leu Leu Phe Thr Pro Val Thr Lys GCC GCT GTG CTA CCG CAA GAA GAA GAA GGC TCG GGT ATG GCC GCC
   Ala Ala Val Leu Pro Gln Glu Glu Glu Gly Ser Gly Met Ala Ala
                                                              1

TGT AAT CTA CCA ATA GTC AGC GGC CCC TGC CGA GCC TTC ATC AAG
   Cys Asn Leu Pro Ile Val Ser Gly Pro Cys Arg Ala Phe Ile Lys
           3'-GAT GGT TAT CAG TCG CCG GGG ACG GCT-5'
                R11S primer              3'-ACG GCT CGG AAG TAG TTC
                                                         Q19K primer
              5                   10                  15

CTC TGG GCA TTT GAT GCT GTC AAG GGG AAG TGC GTC CTC TTC CCC
   Leu Trp Ala Phe Asp Ala Val Lys Gly Lys Cys Val Leu Phe Pro
   GAG ACC CGT-5'
              20                  25                  30

Y46D primer
                        5'- GGG AAC AAG TTC GAC TCA GAG AAG
   TAC GGG GGC TGC CAG GGC AAC GGG AAC AAG TTC GAC TCA GAG AAG
   Tyr Gly Gly Cys Gln Gly Asn Gly Asn Lys Phe Asp Ser Glu Lys
                  35                  40                  45

G-3'
   GAG TGC AGA GAG TAC TGC GGT GTC CCT GGT GAT GGT GAT GAG GAG
   Glu Cys Arg Glu Tyr Cys Gly Val Pro Gly Asp Gly Asp Glu Glu
                  50                  55                  60

BamHI
   CTG CTG CGC TTC TCC AAC TGA CAACTGGATCCTCTACGCCGGAACGCATCGT
   Leu Leu Arg Phe Ser Asn ...       3'- GAGATGCGGCCTTGCGTAGCA-5'
       65              68                     pBRBamHI primer
```

DNA FRAGMENT, VECTOR CONTAINING THE DNA FRAGMENT, TRANSFORMANT TRANSFORMED WITH THE VECTOR AND PROCESS FOR PRODUCING PROTEIN USING THE VECTOR

FIELD OF THE INVENTION

This invention relates to a DNA fragment which is useful when protein is produced making use of recombinant DNA techniques, a vector containing the DNA fragment, a transformant transformed with the vector and a process for the production of protein using the transformant.

BACKGROUND OF THE INVENTION

Genetic engineering techniques are commonly used as a means for the production of proteins such as physiologically active substances and the like. That is, a gene coding for a protein of interest is inserted into an appropriate expression vector, host cells are transformed with the vector and the protein is purified from a cultured mixture of the resulting transformant. In recent years, improvements of such techniques have been made for more efficient production of protein with increased final production yield.

For example, when *Escherichia coli* is used as a host, the expression level of a protein of interest and its final production yield can be increased by using a strong Shine-Dalgano (SD) sequence in order to enhance binding of mRNA to ribosomes (J. Shine and L. Dalgano; *Proc. Natl. Acad. Sci. USA*, vol.71, p.1342, 1974), increasing the copy number of recombinant DNA molecules per cell (R. Nagarajarao and S. G. Rogers; *Gene*, vol.6, p.247, 1978), using a strong promoter with the aim of increasing transcription efficiency (H. A. DeBore, L. J. Comstock and M. Vasser; *Proc. Natl. Acad. Sci. USA*, vol.80, p.21, 1980) or using a protease defective strain (lon⁻ strain for instance) as a host cell in order to prevent hydrolysis of a useful protein of interest by a protease which exists in *E. coli* itself (M. F. Charatte, G. W. Henderson and A. Markovitz; *Proc. Natl. Acad. Sci. USA*, vol.78, p.4728, 1981: C. H. Chung and A. L. Goldberg; *Proc. Natl. Acad. Sci. USA*, vol.78, p.4931, 1981).

On the other hand, processes for the secretion of a protein of interest from its host cells into the extracellular milieu have already been developed and applied to the production of proteins of interest. Such extracellular secretion can avoid decomposition and modification of the protein of interest inside the host cells. In addition, since formation of inclusion bodies can be avoided, purification of the protein of interest can be performed easily. Therefore, techniques for extracellular secretion of a protein of interest are important for increasing production efficiency of the protein by recombinant DNA techniques.

In order to effect extracellular secretion of a protein of interest, it is necessary to express it in the form of an intracellular precursor protein in which a signal peptide composed of approximately 20 to 40 amino acids is attached to the N-terminal of the protein of interest. The term "signal peptide" as used herein means a secretory protein's signal peptide inherent in corresponding host cells. Extracellular secretion of many types of protein by the use of various signal peptides has been reported (K. Nakamura and M. Inouye; *EMBO J.*, vol.1, p.771, 1982: M. Watanabe, Y. Kikuchi, K. Yoda, I. Hinoshita, M. Yamazaki and G. Tamura, Abstracts of Papers, Annual Meeting of Agric. Chem. Soc., Jpn., 1984, p.425).

In general, however, the amount of protein which is expressed and secreted into the extracellular milieu is rather small in comparison with the case of its accumulation in host cells. Because of this, production of protein by means of extracellular secretion is not yet fully applied to industrial processes, in spite of the aforementioned advantages.

Thus, since genetic engineering techniques for the production of protein are not satisfactory yet as described in the foregoing, great concern has been directed toward the development of techniques for use in the improvement of protein productivity, namely improvement of its expression and secretion quantity.

SUMMARY OF THE INVENTION

In view of the above, it therefore becomes an object of the present invention to provide a DNA fragment and a vector containing the fragment, which are useful for the improvement of the productivity of a protein of interest when it is produced by means of genetic engineering techniques using a transformant.

As a result of intensive studies, the inventors of the present invention have found that when the protein of interest is expressed in the form of a fusion protein with a polypeptide having a specified amino acid sequence, its secretion from the host cell is enhanced and its expression quantity also increases. The present invention has been accomplished on the basis of these findings.

According to a first aspect of the present invention, there is provided a DNA fragment containing a nucleotide sequence coding for a specified polypeptide, which is useful for the expression of a protein of interest in the form of a fusion protein with the specified polypeptide.

According to a second aspect of the present invention, there is provided a vector which contains nucleotide sequence encording the polypeptide of the first aspect of the present invention.

According to a third aspect of the present invention, there is provided a transformant transformed with the vector of the second aspect of the present invention.

According to a fourth aspect of the present invention, there is provided a process for the production of a protein of interest in which the vector of the second aspect of the present invention is used.

Other objects and advantages of the present invention will be made apparent as the description progresses.

BRIEF DESCRIPTION OF THE DRAWINGS

FIG. 5 shows the partial nucleotide sequence of a plasmid pM474 from its HindIII recognition site to BamHI recognition site, and its corresponding amino acid sequence (SEQ. I.D. NOS.: 26 and 27).

FIG. 10 shows the nucleotide sequence of a DNA fragment 1b (SEQ. I.D. NO.: 55).

FIG. 11 shows a partial nucleotide sequence of a plasmid pM710 from its HindIII recognition site to BamHI recognition site, and its corresponding amino acid sequence (SEQ. I.D. NOS.: 34 and 35).

FIG. 12 shows the nucleotide sequence of a DNA fragment 2 (SEQ. I.D. NO.: 56).

FIG. 13 shows the nucleotide sequence of a DNA fragment 3 (SEQ. I.D. NO.: 57).

FIG. 14 shows the nucleotide sequence of a DNA fragment 4 (SEQ. I.D. NO.: 58).

FIG. 15 shows the nucleotide sequence of a DNA fragment 5 (SEQ. I.D. NO.: 59).

FIG. 16 shows the nucleotide sequence of a DNA fragment 6 (SEQ. I.D. NO.: 60).

FIG. 17 shows the nucleotide sequence of a DNA fragment 7 (SEQ. I.D. NO.: 61).

FIG. 18 shows the nucleotide sequence of a DNA fragment 8 (SEQ. I.D. NO.: 62).

FIG. 20 shows the nucleotide sequence of a Y46D primer (SEQ. I.D. NO.: 63).

FIG. 21 shows the nucleotide sequence of a Q19K primer (SEQ. I.D. NO.: 64).

FIG. 22 shows the a partial nucleotide sequence of a plasmid pM727 from its HindIII cut site to BamHI cut site, and its corresponding amino acid sequence (SEQ. I.D. NOS.: 30 and 31).

FIG. 23 shows the nucleotide sequence of an R11S primer (SEQ. I.D. NO.: 65).

FIG. 24 shows a partial nucleotide sequence of a plasmid pM765 from its HindIII recognition site to BamHI recognition site, and its corresponding amino acid sequence (SEQ. I.D. NOS.: 32 and 33).

DETAILED DESCRIPTION OF THE INVENTION

Figures 1, 2:
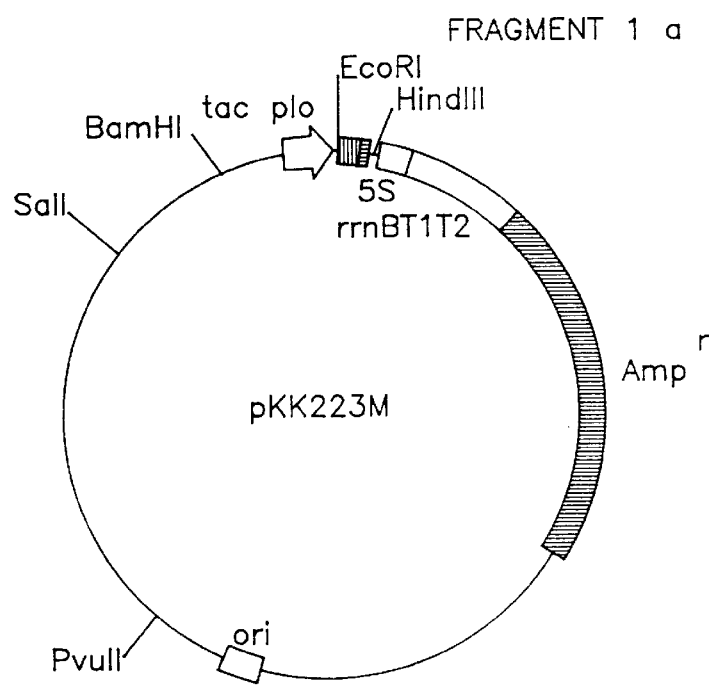
FIG. 1 shows the nucleotide sequence of a DNA fragment 1a (SEQ. I.D. NO.: 50).
FIG. 2 is a map of a plasmid pKK223M.

In the present specification, amino acids are shown by commonly used three letter or single letter codes as summarized below. Unless otherwise noted, an amino acid having optical isomers represents L form, and the left side and right side terminals of each amino acid sequence respectively represent N- and C-terminals.

Gin or Q: glutamine residue
Asp or D: aspartic acid residue
Pro or P: proline residue
Tyr or Y: tyrosine residue
Val or V: valine residue
Lys or K: lysine residue
Glu or E: glutamic acid residue
Ala or A: alanine residue
Asn or N: asparagine residue
Leu or L: leucine residue
Phe or F: phenylalanine residue
Gly or G: glycine residue
His or H: histidine residue
Ser or S: serine residue
Thr or T: threonine residue
Ile or I: isoleucine residue
Trp or W: tryptophan residue
Arg or R: arginine residue
Met or M: methionine residue
Cys or C: cysteine residue In the same manner, each nucleotide sequence is shown herein using the following single letter codes. Unless otherwise noted, the left side and right side terminals of each nucleotide sequence respectively represent 5'- and 3'-ends.

A: adenine
C: cytosine
G: guanine
T: thymidine

The symbols "X, J, Y, Z, x, j, y and z" to be used in this specification will be explained in the following.

The following describes a first aspect of the present invention.

The first aspect of the present invention relates to a DNA fragment which has the nucleotide sequence represented by x.

The small letter "x" represents a nucleotide sequence which encodes the following amino acid sequence. In spite of this small letter "x", hereinafter an amino acid sequence selected from the following 1 to 8 is represeted by the capital letter "X".

Formula 1: AVLPQEEEGSG (Seq. ID No. 2)
Formula 2: AVLPQEEEGSGGGQLVTEVTKKEDSG (Seq. ID No. 4)
Formula 3: AVLDQEEEGSG (Seq. ID No. 6)
Formula 4: AVLPQEEEGDG (Seq. ID No. 8)
Formula 5: AVLPQEEEGSGD (Seq. ID No. 10)
Formula 6: AVLPQEEEGSGDD (Seq. ID No. 12)
Formula 7: AVLPQEEEGSGDDD (Seq. ID No. 14)
Formula 8: ADDPQEEEGSG (Seq. ID No. 16)

Any amino acid sequences selected from the above described formulae 1 to 8 do not coincide with any known signal peptide. But the sequences of the formula 1 coincide with a part of the known protein HI-30 having the molecular weight of 140 kDa. In the sequences of formula 2, 15 amino acids are added to the C-terminal of the sequence of formula 1. In the sequences of formulae 5, 6 and 7, 1 to 3 amino acids are added to the C-terminal of the sequence of formula 1. In the sequences of formulae 3, 4 and 8, one or two amino acids in the sequence of formula 1 are replaced by other amino acids. When a protein of interest is produced as a fusion protein with a polypeptide having any of these modified amino acid sequences of the sequence of formula 1, extracellular secretion of the protein of interest increases similar to the case of its fusion with a polypeptide having the amino acid sequence of formula 1. As will be described later in Example 2, when a protein of interest was produced in the form of a fusion protein with a polypeptide having any of the amino acid sequences of formulae 3, 4, 5 and 6, the polypeptide showed particularly excellent effect on the extracellular expression of the protein of interest.

When these effects are taken into consideration, it is considered that not only the above amino acid sequences of formulae 1 to 8 but also their derivatives obtained for example by partially substituting amino acids in the sequences with other amino acids or adding or deleting optional numbers of optional amino acids to or from the N-terminal and/or C-terminal of each sequence can be used for the increment of the protein productivity. In consequence, derivatives of the amino acid sequences of formulae 1 to 8 in which substitution, deletion or addition of at least one amino acid is generated are also included in the polypeptides represented by the symbol X. And the symbol "x" represents any nucleotide sequence which encodes any of the amino acid sequences of the formulae 1 to 8 and their derivatives mentioned above. Taking the degeneracy of codon into consideration, the nucleotide sequences represented by x should be considered including all possible combinations of codons.

Most preferred illustrative example of the nucleotide sequence represented by the symbol x is at least one sequence selected from the following formulae 9 to 16 which correspond respectively to the Sequence ID Nos. 1, 3, 5, 7, 9, 11, 13 and 15 of the SEQUENCE LISTING attached hereto.

The following describes a second aspect of the present invention. Meaning and preferred examples of the symbols X, x used in the following are as described in the foregoing.

The second aspect of the present invention relates to a vector which contains the nucleotide sequence represented by x. Since the nucleotide sequence represented by x is effective in increasing protein productivity, the vector of the present invention can be used as a tool for the construction of protein expression vectors or the production of a protein of interest.

Preferably, the vector of the present invention may have another sequence represented by j which is coding for an

| Formula 9  | GCT | GTG | CTA | CCG | CAA | GAA | GAA | GAA | GGC | TCG | GGT |     |     |     |
|------------|-----|-----|-----|-----|-----|-----|-----|-----|-----|-----|-----|-----|-----|-----|
| Formula 10 | GCT | GTG | CTA | CCC | CAA | GAA | GAG | GAA | GGA | TCA | GGG | GGT | GGG | CAA |
|            | CTG | GTA | ACT | GAA | GTC | ACC | AAG | AAA | GAA | GAC | TCG | GGT |     |     |
| Formula 11 | GCT | GTG | CTA | GAT | CAA | GAA | GAA | GAA | GGC | TCG | GGT |     |     |     |
| Formula 12 | GCT | GTG | CTA | CCG | CAA | GAA | GAA | GAA | GGC | GAT | GGT |     |     |     |
| Formula 13 | GCT | GTG | CTA | CCG | CAA | GAA | GAA | GAA | GGC | TCG | GGT | GAT |     |     |
| Formula 14 | GCT | GTG | CTA | CCG | CAA | GAA | GAA | GAA | GGC | TCG | GGT | GAT | GAT |     |
| Formula 15 | GCT | GTG | CTA | CCG | CAA | GAA | GAA | GAA | GGC | TCG | GGT | GAT | GAT | GAT |
| Formula 16 | GCT | GAC | GAC | CCG | CAA | GAA | GAA | GAA | GGC | TCG | GGT |     |     |     |

The DNA fragment of the present invention may also has a restriction enzyme recognition site and a nucleotide sequence which encodes an optional amino acid or amino acid sequence, linked to the 5' and 3' ends of the nucleotide sequence x. For example, a DNA fragment having on its 5' end a nucleotide sequence coding for a signal sequence represented by j, namely a DNA fragment having a nucleotide sequence which encodes an amino acid sequence J-X (cf. SEQ. I.D. NOS.: 35, 37, 39, 41, 43, 35, 47, and 49 in SEQUENCE LISTING), can be used for construction of an expression vector. Also preferred are DNA fragments represented by j-x-y, j-x-y-z and j-x-z.

The detailed descriptions represented by the symbols j, y and z will be described in the following second aspect of the present invention.

The DNA fragment of the present invention can be obtained by various means. For example, when the fragment is prepared by chemical synthesis, a nucleotide sequence of interest and its complementary DNA are designed as single-stranded DNA fragments. Next, each of the thus designed oligomers is chemically synthesized and purified using a DNA synthesizer (for example, Model 394A manufactured by Applied Biosystems). The thus synthesized oilgomers are then subjected to necessary treatments including 5' end phosphorylation with T4 polynucleotide kinase, annealing and ligation with T4 DNA ligase or the like. Alternatively, the DNA fragment may be obtained from an appropriate cDNA library by PCR (Polymerase Chain Reaction) or the hybridization using chemically synthesized primers. ("PCR protocols, A Guide to Methods and Applications edited by Michael, A. I. et al., Academic Press, 1990", and "Molecular Cloning, A laboratory Manual, edited by T. Maniatis et al., Cold Spring harbor Laboratory, 1982. A DNA fragment having a desired mutation may also be obtained from an appropriate cDNA library by PCR (Landt, O et al., Gene, vol. 96, pp. 125–128, 1990)).

When a protein of interest is expressed in the form of a fusion protein with a polypeptide having the amino acid sequence of X, at least its expression and/or secretion quantity increases. The DNA fragment of the first aspect of the present invention is useful when a protein of interest to be produced making use of recombinant DNA techniques is expressed in the form of a fusion protein with a polypeptide having the amino acid sequence of X, that is, the inventive DNA fragment is useful for high yield production of the protein of interest.

amino acid sequence represented by the symbol "J". The symbol "J" represents amino acid sequence of a signal peptide and the symbol "j" represents its corresponding nucleotide sequence.

The term "signal peptide" as used herein means every signal peptide of all types of secretory proteins originated from either procaryotic or eucaryotic organisms. Preferably, the signal peptide represented by the symbol "J" can be operated in a host cell using for a production of a protein of interest. Illustrative examples of commonly used signal peptides include those of *Escherichia coli* outer membrane lipoprotein (Lpp), *E. coli* outer membrane protein (OmpF), λ phage receptor protein (LamB) and the like. Though not particularly limited, signal peptide of *E. coli* alkaline phosphatase may be used preferably as the signal peptide J of the present invention. Amino acid sequence of the signal peptide of *E. coli* alkaline phosphatase is shown below (this formula corresponds to the SEQ. I.D. NO.: 18 of the SEQUENCE LISTING)

Formula 17

MKQSTIALALLPLLFTPVTKA

The symbol "j" represents any nucleotide sequence which encodes any of the signal peptides represented by the symbol J. As is commonly known, the degeneracy of codons exist corresponding to each amino acid. In consequence, all possible combinations of codons taking degeneracy of codon into consideration are included in the nucleotide sequence represented by the symbol j.

Most preferred illustrative example of the nucleotide sequence j is shown by the following formula 18 which corresponds to the SEQ. I.D. NO.: 17 of the SEQUENCE LISTING.

Formula 18

ATG AAA CAA AGT ACT ATT GCA CTG GCA CTC TTA CCG TTA CTG TTT ACC CCT GTG ACA AAG GCC

The sequence represented by j is bound to the 5' end of the sequence represented by x to obtain a vector having a nucleotide sequence represented by j-x.

As well known, for the secretion of a protein of interest, the protein must be expressed in the form of the protein which is bound to a signal peptide. However, any proteins can not be secreted even in the form of the protein which is bound to a signal peptide.

When a protein of interest is expressed in the form of a fusion protein with X to obtain a polypeptide having the amino acid sequence of J-X-a protein of interest, the extracellular secretion quantity and/or expression quantity of the protein is much higher than the polypeptide having the amino acid sequence of J-a protein of interest when the protein of interest is bound directly to the signal peptide J. In consequence, the nucleotide sequence represented by j-x is useful at least in increasing the expression and/or secretion level. A vector containing the nucleotide sequence of j-x can be used as a tool for the construction of expression vectors.

The vector of the present invention may have a restriction enzyme recognition site attached to the 5' and/or 3' end of the j-x sequence. Such a vector is useful when the nucleotide sequence represented by j-x is inserted into an appropriate commercially available vector or when a nucleotide sequence coding for an optional protein of interest is inserted into a downstream position of the j-x sequence.

The vector of the present invention may have a nucleotide sequence represented by y which codes for an amino acide sequence represented by Y bound to the 3' end of the j-x sequence, namely a vector containing a sequence represented by j-x-y. The symbol "Y" as used herein means an amino acid or an amino acid sequence which can be recognized and cleaved by chemical compounds, enzymes and the like, and the term "y" means its corresponding nucleotide sequence.

When a protein of interest is produced in the form of a fusion protein with other protein, it is necessary to cut and separate these two proteins from each other. For this purpose, certain chemical compounds and enzymes are used which can cleave a polypeptide at a specific position of its amino acid sequence. Illustrative examples of such chemicals include cyanogen bromide, an acid, 2-(2-nitrophenylsulphonyl)-3-methyl-3-bromoindolenine (BNPS-skatole), hydroxylamine and the like. Illustrative examples of enzymes for use in the site-specific digestion include enterokinase, trypsin, blood coagulation factor Xa, collagenase, thrombin and the like.

The symbol Y may be any amino acid or amino acid sequence which is recognized and cleaved by such chemical compounds or enzymes, such as Met which is recognized by cyanogen bromide, Lys or Arg which is recognized by trypsin and an amino acid sequence Ile-Glu-Gly-Arg (SEQ. I.D. NO.: 19) which is recognized by blood coagulation factor Xa (cf. *Biotrend*, vol.2 No.4, p.111, 1990, Maruzen). It may be selected at will from these amino acids or amino acid sequences. The symbol "y" represents any nucleotide sequence which encodes any of the amino acids or amino acid sequences represented by the symbol Y. As is commonly known the degeneracy of codons exist corresponding to each amino acid. In consequence, all possible combinations of codons taking degeneracy of codon into consideration are included in the nucleotide sequence represented by the symbol y. Most preferred illustrative examples of y include ATG which encodes Met and a sequence coding for Ile-Glu-Gly-Arg (SEQ. I.D. NO.: 19) which is recognized by FXa.

The vector of the present invention may have a restriction enzyme recognition site attached to the 5' and/or 3' end of the j-x-y sequence. Such a vector is useful when the nucleotide sequence represented by j-x-y is inserted into an appropriate commercially available vector or when a nucleotide sequence coding for an optional protein of interest is inserted into a downstream position of the j-x-y sequence.

The vector of the present invention may also have a nucleotide sequence coding for an optional protein of interest attached to the 3' end of the j-x or j-x-y sequence, namely a vector which contains a nucleotide sequence represented by j-x-z or j-x-y-z. The symbol "Z" as used herein means amino acid sequence of a protein of interest and the symbol "z" means its corresponding nucleotide sequence.

The protein of interest represented by Z includes not only human derived proteins but also other proteins of any origin having various biochemical and physical properties. Illustrative examples of such proteins include interleukins 1 to 11, various colony-stimulating factors, cytokines such as TNF, IFNα, IFNβ, IFNγ and the like, growth factors such as EGF, FGF and the like, hormones such as insulin and the like, enzymes such as t-PA and the like, or inhibitors and receptors thereof, and biological components such as collagen and the like. Though not particularly limited, proteins having physiological activities are preferred as the protein of interest represented by the symbol Z, more preferred examples including proteins having the amino acid sequences of the following formulae 19 to 22, as well as derivatives of these proteins in which substitution, addition or deletion of at least one amino acid is generated in their amino acid sequences. Formula 19 represents amino acid sequence of PSTI (pancreatic secretory trypsin inhibitor; Kikuchi N. et al., *J. Biochem.*, vol.102, pp.607–612, 1987), formula 20 represents AN68 (Japanese Patent Application No. 4-119289), formula 21 represents Q19K/Y46D (Japanese Patent Application No. 4-297344) and formula 22 represents R11S/Q19K/Y46D (Japanese Patent Application No. 4-297344). These proteins are described in detail in the respective publication and patent applications, and these descriptions are incorporated herein by references.

Formula 19 (SEQ I.D. NO.:20)

| Asp | Ser | Leu | Gly | Arg | Glu | Ala | Lys | Cys | Tyr |
|-----|-----|-----|-----|-----|-----|-----|-----|-----|-----|
| Asn | Glu | Leu | Asn | Gly | Cys | Thy | Lys | Ile | Tyr |
| Asp | Pro | Val | Cys | Gly | Thr | Asp | Gly | Asn | Thr |
| Tyr | Pro | Asn | Glu | Cys | Val | Leu | Cys | Phe | Glu |
| Asn | Arg | Lys | Arg | Gln | Thr | Ser | Ile | Leu | Ile |
| Gln | Lys | Ser | Gly | Pro | Cys |     |     |     |     |

Formula 20 (SEQ I.D. NO.:21)

| Ala | Ala | Cys | Asn | Leu | Pro | Ile | Val | Arg | Gly |
|-----|-----|-----|-----|-----|-----|-----|-----|-----|-----|
| Pro | Cys | Arg | Ala | Phe | Ile | Gln | Leu | Trp | Ala |
| Phe | Asp | Ala | Val | Lys | Gly | Lys | Cys | Val | Leu |
| Phe | Pro | Tyr | Gly | Gly | Cys | Gln | Gly | Asn | Gly |
| Asn | Lys | Phe | Tyr | Ser | Glu | Lys | Glu | Cys | Arg |
| Glu | Tyr | Cys | Gly | Val | Pro | Gly | Asp | Gly | Asp |
| Glu | Glu | Leu | Leu | Arg | Phe | Ser | Asn |     |     |

Formula 21 SEQ I.D. NO.: 22)

| Ala | Ala | Cys | Asn | Leu | Pro | Ile | Val | Arg | Gly |
|-----|-----|-----|-----|-----|-----|-----|-----|-----|-----|
| Pro | Cys | Arg | Ala | Phe | Ile | Lys | Leu | Trp | Ala |
| Phe | Asp | Ala | Val | Lys | Gly | Lys | Cys | Val | Leu |
| Phe | Pro | Tyr | Gly | Gly | Cys | Gln | Gly | Asn | Gly |
| Asn | Lys | Phe | Asp | Ser | Glu | Lys | Glu | Cys | Arg |
| Glu | Tyr | Cys | Gly | Val | Pro | Gly | Asp | Gly | Asp |
| Glu | Glu | Leu | Leu | Arg | Phe | Ser | Asn |     |     |

Formula 22 (SEQ I.D. NO.: 23)

| Ala | Ala | Cys | Asn | Leu | Pro | Ile | Val | Ser | Gly |
|-----|-----|-----|-----|-----|-----|-----|-----|-----|-----|
| Pro | Cys | Arg | Ala | Phe | Ile | Lys | Leu | Trp | Ala |
| Phe | Asp | Ala | Val | Lys | Gly | Lys | Cys | Val | Leu |
| Phe | Pro | Tyr | Gly | Gly | Cys | Gln | Gly | Asn | Gly |
| Asn | Lys | Phe | Asp | Ser | Glu | Lys | Glu | Cys | Arg |
| Glu | Tyr | Cys | Gly | Val | Pro | Gly | Asp | Gly | Asp |
| Glu | Glu | Leu | Leu | Arg | Phe | Ser | Asn |     |     |

In that case, the amino acid or amino acid sequence Y which is recognized by a chemical compound or an enzyme may preferably be an amino acid or amino acid sequence that does not exist in the protein of interest represented by Z. It is preferable therefore that the nucleotide sequence y also encodes such a type of Y.

The fusion protein represented by X-Z or X-Y-Z is extracellular secreted from an appropriate host cell transformed with an expression vector having the nucleotide sequence represented by j-x-z or j-x-y-z.

The vector of the present invention may have another sequence necessary for an expression of a protein of interest, a promoter, a marker sequence, a linker sequence and the like inserted into optional upstream and/or downstream positions of the sequence represented by j-x, j-x-y, j-x-y-z or j-x-z. For example, the vector of the present invention may have at least one promoter sequence and SD sequence inserted into upstream positions of the sequence represented by j-x, j-x-y, j-x-y-z or j-x-z, or a tetracycline, kanamycin or ampicillin resistant gene in an optional upstream or downstream position of the sequence. The vector may also be contain a sequence of dehydrofolate reductase (DHFR) gene or the like, for the purpose of amplifying plasmid copy numbers.

The vector of the present invention described above may be used for any purpose. For example, it may be used for the cloning of a gene or as a tool for the construction of other expression vector.

Preferably, the vector of the present invention may have a self-replication function. As has been described in the foregoing in relation to the first aspect of the present invention, the nucleotide sequence represented by x is useful at least in increasing expression and/or secretion quantity of protein. In consequence, the vector of the present invention containing the nucleotide sequence of x is used preferably for the expression of protein. That is, it is preferable to insert at least a promoter sequence into the vector of the present invention in addition to the j-x, j-x-y, j-x-y-z or j-x-z sequence. More preferably, it may contain not only a promoter sequence but also an operator sequence and an SD sequence.

Illustrative examples of promoters which function in procaryotic host cells include trp promoter, lac promoter, λ phage $P_L$ promoter, tac promoter, bla promoter, lpp promoter, ompA promoter, ompC promoter, ompF promoter and the like. Illustrative examples of promoters which function in eucaryotic host cells include actin gene promoter, SV40 promoter, adenovirus II promoter, elongation factor gene promoter and the like.

Though not particularly limited, the promoter sequence to be contained in the vector of the present invention may be at least one sequence selected preferably from those of trp promoter, tac promoter and lac promoter.

The vector of the second aspect of the present invention can be obtained by various methods. For example, it may be obtained by preparing a double-stranded DNA fragment composed of a nucleotide sequence of j-x, j-x-y, j-x-z or j-x-y-z and its complementary sequence and then inserting the thus prepared fragment into a commercially available vector with correct reading frame. The DNA fragment having a nucleotide sequence of for example j-x, j-x-y, j-x-z or j-x-y-z can be obtained by known DNA techniques. For example, it may be synthesized chemically or prepared by PCR or the like means using an appropriate DNA fragment as a template. As a matter of course, it may be obtained by preparing DNA fragments respectively having nucleotide sequences of j, x, y and z and then ligating the fragments. Since the signal peptide j is contained in some commercially available vectors in appropriate sequences, it can be obtained by digesting the vectors with proper restriction enzymes. Also, together with the double-stranded DNA fragment prepared above, other DNA fragments having proper promoter and marker sequences may be prepared respectively and inserted into optional regions of a commercial vector. Insertion of the DNA fragment into a vector can be made by known techniques disclosed for instance in *Molecular Cloning, A Laboratory Manual*, ed. by T. Maniatis et al., Cold Spring Harbor Laboratory, 1982. The vector to be used is not particularly limited and can be selected from various plasmid vectors, phage vectors and virus vectors. Typical examples of such vectors include pUC118, pBluescript II KS(+), pBR322, pSV2-dhfr, λZapII, λgt10, pAc700, AcNPV, YAC, pEFBOS, pEFN-II and the like.

Next, a transformant of a third aspect of the present invention is described.

The transformant of the third aspect of the present invention is obtained by transforming an appropriate animal or microbial host cells with the vector of the second aspect of the present invention. Examples of such host cells include *E. coli* cells, *Bacillus subtilis* cells, yeast cells, COS cells, CHO cells, BHK cells, Sf cells, HeLa cells, Namalwa cells and the like. Temperature sensitive, auxotrophic and the like mutants of these cells can also be used as host cells for the isolation of the transformant of the present invention. Though not particularly limited, the transformant of the present invention may be obtained preferably from at least one host selected from *E. coli, B. subtilis* and yeast.

Preferably, the transformant of the present invention is capable of expressing and producing a protein of interest. In that case, the vector to be used in the transformation should contain promoter and the like sequences necessary for the protein expression, and such sequences should be selected depending on the host cells to be used in such a combination that they can function each other. Typical examples are a combination of a vector containing SV40 early promoter with COS cells and a combination of a vector containing trp promoter and tryptophan SD sequence with *E. coli* cells (cf. *Idenshi Kogaku Handbook* (Gene Engineering Handbook), a special number of *Jikken Igaku* (Experimental Medicine), published by Yodo-sha on Mar. 20, 1991).

Methods for the preparation of transformants are well known (cf. *Idenshi Kogaku Handbook*, op.cit.). That is, host cells are transformed with the vector of the second aspect of the present invention by a proper known means such as electroporation, protoplast transformation, alkali metal treatment, calcium phosphate gel method, DEAE dextran method, microinjection or infection with virus particles. Thereafter, a clone is selected from the host cells thus transformed with the vector making use of a marker such as a drug resistance, an auxotrophic property or the expressed product.

The transformant of the third aspect of the present invention can be used for the preparation of a large quantity of the vector of the second aspect of the present invention and for the production of a protein of interest.

Next, a process for the production of a protein of interest is described as a fourth aspect of the present invention.

Meaning and preferred examples of the symbols X, J, Y, Z, x, j, y and z used in the following are as described in the foregoing.

The fourth aspect of the present invention is a process for the production of protein making use of the DNA fragment of the first aspect of the present invention, namely a process for the production of protein making use of the vector of the second aspect of the present invention. This process is characterized by the use of a step in which a protein of interest Z is expressed as a fusion protein having an amino acid sequence represented by either J-X-Z or J-X-Y-Z. In other words, in the production process of the present invention, the protein of interest Z expressed as a fusion protein having an amino acid sequence of J-X or J-X-Y on its N-terminal may be present in the host cells or cultured medium as it is or in the form of X-Z, X-Y-Z, Z or the like resulting from the removal of the signal peptide. The protein of interest may be isolated and purified in the form of a single protein or a fusion protein.

The following describes an example of the production process of the present invention.

The inventive production process can be effected for example by carrying out the following steps a) to e) in that order.

a) An expression vector containing a DNA fragment represented by j-x-z or j-x-y-z is prepared.
b) Appropriate host cells are transformed with the expression vector obtained in the above step a).
c) The thus obtained transformant is cultured, if necessary inducing expression of the introduced gene.
d) A fusion protein having an amino acid sequence represented by J-X-Z or J-X-Y-Z is recovered and purified from the resulting culture or cells of the transformant.
e) The protein of interest Z is isolated and purified from the thus obtained fusion protein.

The expression vector of the above step a) is the vector of the second aspect of the present invention which contains necessary nucleotide sequences for the protein expression. Method for the preparation of this vector was described in the foregoing in relation to the second aspect of the present invention.

In the step b), a transformant is prepared using appropriate host cells in which the expression vector obtained in the step a) can perform its function. Method for the transformation of host cells was described in the foregoing in relation to the third aspect of the present invention.

In the above step c), the transformant is cultured by a proper culturing method depending on the used host cells (cf. S. Aiba et al., *Seibutsu Kagaku Kogaku* (Biochemical Engineering), 1976, Tokyo University Press; T. Ishikawa, *Biseibutsu Idengaku Jikken-ho* (Methods for Microbial Genetics), pp.96–115, 1982, Kyoritsu Shuppan). In general, *E. coil* cells are cultured in L-broth or M9CA medium (containing casamino acid) at 37° C. for 1 to 2 days using a jar fermenter. In the case of *B. subtilis*, it may be cultured at 30° to 35° C. for 1 to 2 days on TBAB (Tryptose Blood Agar Base, manufactured by Difco) plate medium or in Penassay broth (Antibiotic Medium No. 3, Difco). When a yeast strain is used, it may be cultured in YP medium containing 8% sucrose at 28° C. for about 1 to 2 days.

If necessary, the recently developed low temperature culture method may be used in which a transformant is cultured at a low temperature (approximately 20° to 25° C.) in order to further increase expression or secretion quantity of a protein of interest. Combined use of such an effective culture method in increasing protein productivity and the production process of the present invention will result in further high final productivity of the protein of interest.

Necessity for the expression-inducing stimulation and its methodology may be decided depending on the type of promoter contained in the vector. For example, when the promoter is tryptophan promoter, the expression-inducing stimulation may be carried out by adding 3β-indoleacrylic acid to M9 medium (minimum essential medium). In other words, in the protein production process of the present invention, the expression inducing stimulation may be carried out depending on each expression vector used in transformation and the resulting transformant.

In the above step d), a fusion protein having an amino acid sequence represented by J-X-Z or J-X-Y-Z is recovered and purified. In general, a protein having a signal peptide is secreted from host cells into the extracellular milieu, but sometimes accumulated in the host cells in the form of inclusion body.

When the protein of interest is to be recovered from a culture, its purification is carried out using the culture supernatant or its concentrate as the starting material. When a protein of interest is accumulated in the periplasm of host cells, purification of the protein is carried out after recovering it from the cells by an appropriate method such as of Willsky et al. (*J. Bacteriol.*, vol.1, p.595, 1976). When a fusion protein accumulated in host cells is recovered, the cells are disrupted by lysozyme treatment, surfactant treatment, freeze-thawing, pressurization or the like means and then the fusion protein is extracted by centrifugation, filtration or the like means. The thus extracted fusion protein is subjected to refolding (cf. Thomas E. Creighton, *J. Mol. Biol.*, vol.87, pp.563–577, 1974) and then purified.

Examples of commonly used protein purification techniques include ammonium sulfate precipitation, ultrafiltration, isoelectric precipitation, gel filtration, electrophoresis, ion exchange chromatography, hydrophobic chromatography, various types of affinity chromatography such as antibody chromatography and the like, chromatofocusing, adsorption chromatography, reverse phase chromatography and the like. In the step d), therefore, purification of a fusion protein of interest may be carried out making use of its molecular weight and physiological activities as markers, by the use of commonly used purification techniques in optional combination of an appropriate order and employing an HPLC system and the like as occasion demands.

In the above step e), the protein of interest Z is isolated and purified from the thus obtained fusion protein. When the fusion protein is recovered from a culture supernatant or a periplasmic fraction in the above step d), the resulting protein may already be free from the signal peptide portion represented by J. In that case, the object of the step e) is attained by digesting and removing the other portion represented by X or X-Y. When the fusion protein is recovered from cultured cells, a portion represented by J-X or J-X-Y is digested and removed from the recovered protein.

The digestion removal is carried out making use of a chemical compound or enzyme which can recognize a specific amino acid or amino acid sequence (an amino acid or amino acid sequence represented by Y when the fusion protein is J-X-Y-Z) and react with the recognized portion, thereby effecting cutting of the polypeptide chain. Though the chemical compound or enzyme is not particularly limited, it is necessary to select a substance which does not spoil the activity of the protein of interest Z. Though it is preferable to isolate the protein of interest Z with its complete amino acid sequence, the protein may have a partial deletion in its N- and/or C-terminal side caused by the chemical compound or enzyme treatment, provided that such a deletion does not spoil its activity and properties. In the same manner, the protein of interest Z may have a residual peptide fragment of X or Y in its N-terminal side.

As a matter of course, the digestion treatment with a chemical compound or enzyme is not necessary when the J-X or J-X-Y portion has been removed by host cells themselves from the fusion protein expressed by the transformant in the form of J-X-Z or J-X-Y-Z.

EXAMPLES

Examples of the present invention are given below by way of illustration and not by way of limitation. Abbreviations used herein are based on idiomatical expressions. Experiments were carried out in the light of the following reports and books.

1. *A Practical Guide to Molecular Cloning*; Bernard Perbal, 1984, John Wiley & Sons, Inc.
2. *A Practical Guide to Molecular Cloning*; Second edition, Bernard Perbal, 1984, John Wiley & Sons, Inc.
3. Idenshi Sosa Jikken-ho (*Gene Manipulation Techniques*); Y. Takagi, 1980, Kodansha
4. Idenshi Sosa Manual (*Gene Manipulation Manual*); Y. Takagi, 1980, Kodansha
5. *Molecular Cloning, A Laboratory Manual*; T. Maniatis et al., 1982, Cold Spring Harbor Laboratory
6. *Methods in Enzymology*; vol.65, L. Grossman et al., 1980, Academic Press
7. *Methods in Enzymology*; vol.68, R. Wu, 1979, Academic Press
8. *PCR Protocols, A Guide to Methods and Applications*; Michadel, A. I. et al., 1990, Academic Press
9. *Molecular Cloning, A Laboratory Manual*; Second edition, T. Maniatis et al., 1989, Cold Spring Harbor Laboratory
10. *Saibokogaku-teki Gijutsu Soshu-hen* (Cell Technology Review), a supplement of *Jikken Igaku* (Experimental Medicine), 1989, Yodo-sha
11. *Idenshi Kogaku Handbook* (Gene Engineering Handbook), a supplement of *Jikken Igaku* (Experimental Medicine), 1991, Yodo-sha

Example 1 Preparation of plasmid pKK223M

The following experiments were carried out in order to prepare a plasmid pKK223M which is a vector containing a nucleotide sequence represented by j-x wherein j is a nucleotide sequence coding for the E. coli alkaline phosphatase signal sequence of the aforementioned formula 18 and x is the nucleotide sequence of the aforementioned formula 9.

Firstly, a commercially available plasmid pKK223-3 was double-digested with restriction enzymes EcoRI and HindIII, the thus obtained mixture of DNA fragments was subjected to 0.7% agarose gel electrophoresis and then a DNA fragment of about 4.5 kb was separated from other DNA fragments by adsorbing it to a sheet of diethylaminoethyl cellulose paper (to be referred to as "DEAE cellulose paper" hereinafter). Thereafter, the DEAE cellulose paper was washed with a high concentration salt solution (2M NaCl/10 mM tris-HCl buffer (pH 7.5)/1 mM EDTA) to recover the DNA fragment of about 4.5 kb from the DEAE cellulose paper.

A DNA fragment shown in FIG. 1 (fragment 1a, SEQ. I.D. NO.: 50) was designed by dividing it into 4 fragments. Of these 4 fragments, S2 and S3 were treated with T4 polynucleotide kinase in the presence of ATP to effect phosphorylation of their 5' ends. Next, a pair of oligonucleotides S1 and S3 and another pair of S2 and S4 were subjected to annealing and subsequent ligation with T4 DNA ligase (manufactured by Takara Shuzo Co., Ltd.). A sample after the ligation was subjected to 8% polyacrylamide gel electrophoresis to separate and prepare a DNA fragment of about 120 bp.

Thereafter, the aforementioned DNA fragment of about 4.5 kbp was ligated to the just obtained DNA fragment of about 120 bp. *E. coli* strain HB101 was transformed with the DNA fragment and an ampicillin resistant colony of interest was isolated. A plasmid DNA was separated from the thus obtained transformant and named plasmid pKK223M (see FIG. 2).

Example 2 Preparation of plasmid pM474

A plasmid pM474 of the present invention was prepared in the following manner. This plasmid is a vector containing a nucleotide sequence of j-x-y-z for use in the expression of PSTI, wherein j represents a nucleotide sequence which encodes the *E. coli* alkaline phosphatase signal sequence of the aforementioned formula 18, x represents the nucleotide sequence of the aforementioned formula 9, y represents a nucleotide sequence that encodes Met and z represents a nucleotide sequence which encodes PSTI.

[1] Preparation of plasmid 474

Plasmid pM463 (Kanamori T. et al., *Gene*, vol.66, pp.295–300, 1988; see FIG. 3) was double-digested with restriction enzymes HindIII and NruI to separate a DNA fragment of about 3.4 kb.

Figures 3, 4:
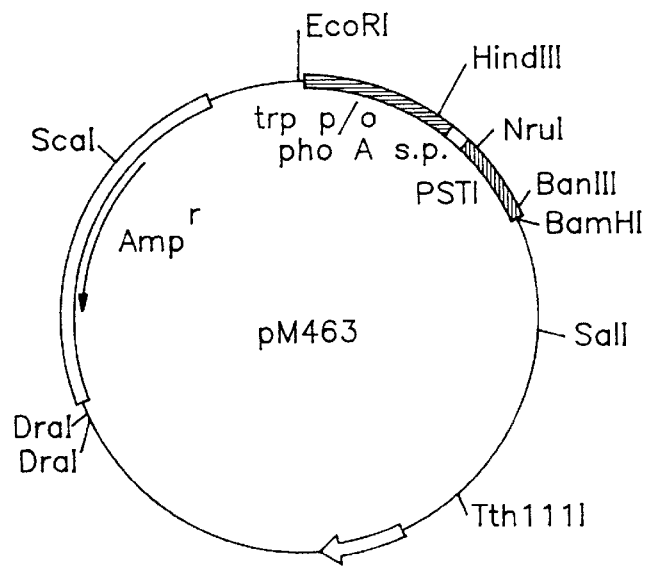
FIG. 3 is a map of a plasmid pM463.
FIG. 4 shows the nucleotide sequence of a DNA fragment A (SEQ. I.D. NO.: 51).

Separately from this, a DNA fragment composed of an SD sequence, a nucleotide sequence coding for the *E. coll* alkaline phosphatase signal peptide, a nucleotide sequence coding for the aforementioned amino acid sequence of formula 1 and a nucleotide sequence coding for a portion of the N-terminal side amino acid sequence of PSTI was designed (fragment A, see FIG. 4 SEQ. I.D. NO.: 51) by dividing it into 6 fragments. The thus divided fragments were chemically synthesized in the same manner as described in Example 1, and a DNA fragment of about 140 bp was finally prepared. Thereafter, the aforementioned DNA fragment of about 3.4 kbp was ligated with the just obtained DNA fragment of about 140 bp. *E. coli* strain HB101 was transformed with the DNA fragment an ampicillin resistant colony of interest was isolated. A plasmid DNA was separated from the thus obtained transformant and named plasmid pM474.

The thus obtained plasmid pM474 was double-digested with restriction enzymes HindIII and BamHI to extract and purify a fragment of interest having a size of about 300 bp. Sequence of the thus obtained fragment was analyzed by a DNA sequencer (DNA Sequencer 370A, manufactured by Applied Biosystems).

The thus confirmed partial nucleotide sequence of plasmid pM474 from its HindIII recognition site to BamHI recognition site and its corresponding amino acid sequence are shown in FIG. 5 (cf. SEQ. I.D. NOS.: 26 and 27).

[2] Comparison of extracellular secretion quantities

Extracellular secretion quantity of PSTI when the plasmid pM474 of the present invention was used was compared with the case of the use of the aforementioned plasmid pM463. In the plasmid pM463, a PSTI-encoding nucleotide sequence is directly ligated to the downstream of a nucleotide sequence which encodes *E. coli* alkaline phosphatase signal peptide.

Firstly, in accordance with the method of Hanahan (Hanahan D., "Techniques for Transformation of *E. coli*", in *DNA Cloning*, vol.1, Glover D. M. (ed.), pp.109–136, IRL Press, 1985), a lon$^-$ strain of *E. coli* GC4670 (lon: Tn10 thr, leu, lacY) was transformed separately with plasmid pM463 and pM474 to obtain *E. coli* transformants GC4670 (pM463) and GC4670 (pM474). Each of the thus obtained transformants was cultured overnight in 5 ml of L-broth containing 50 μg/ml of ampicillin, and the resulting culture was inoculated into 50 volumes of M9CA medium containing 50 μg/ml of ampicillin and 2% of casamino acid and cultured at 37° C. for about 1 hour. To the resulting culture was added 3β-indoleacrylic acid (manufactured by Wako Pure Chemical Industries, Ltd.) to a final concentration of 10 μg/ml. After 16 hours of additional culturing, the thus obtained culture was subjected to centrifugation using a centrifuge (CR20B3, manufactured by Hitachi Koki Co., Ltd.) to recover the culture supernatant.

Each of the thus obtained culture supernatants was serially diluted with 0.1% BSA/0.2M triethanolamine-HCl buffer (pH 7.8) to measure trypsin inhibitory activity by a procedure which will be described later. As the results, markedly high extracellular secretion quantity was found in the case of plasmid pM474 which contains the nucleotide sequence represented by x. The results are shown below.

| Transformant | Trypsin inhibitory activity in culture supernatant | Amount of protein in culture supernatant calculated from specific activity |
|---|---|---|
| GC4670 (pM463) | 311 U/ml | 50 μg/ml |
| GC4670 (pM474) | 827 U/ml | 140 μg/ml |

Example 3

Plasmids were prepared by the following procedures [2] to [9] as vectors for use in the expression of polypeptide AN68, each containing a nucleotide sequence of j-x-y-z wherein j represents a nucleotide sequence which encodes the E. coli alkaline phosphatase signal sequence of the aforementioned formula 18, x represents the nucleotide sequence of the aforementioned formula 9 or 12, y represents a nucleotide sequence that encodes Met and z represents a nucleotide sequence which encodes polypeptide AN68.

Also, a plasmid pM594 in which a polypeptide AN68-encoding nucleotide sequence was directly ligated to a downstream region of a nucleotide sequence which encodes E. coli alkaline phosphatase signal peptide was prepared by the following procedure [1].

[1] Preparation of plasmid pM594

Plasmid pM594 was prepared from plasmid pM552 (cf. Japanese Patent Application No. 3-325220) in the following manner. The plasmid pM552 contains a tryptophan promoter and a Kanamycin resistance gene. It also contains a nucleotide sequence of the following formula 24 which encodes an amino acid sequence of the following formula 23 which is in the downstream of a nucleotide sequence that encodes E. coli alkaline phosphatase signal peptide (FERM BP-3561, see FIG. 6).

Formula 23 (SEQ I.D. NO.:25)

```
Thr  Val  Ala  Ala  Cys  Asn  Leu  Pro  Ile  Val
Arg  Gly  Pro  Cys  Arg  Ala  Phe  Ile  Gln  Leu
Trp  Ala  Phe  Asp  Ala  Val  Lys  Gly  Lys  Cys
Val  Leu  Phe  Pro  Tyr  Gly  Gly  Cys  Gln  Gly
Asn  Gly  Asn  Lys  Phe  Tyr  Ser  Glu  Lys  Glu
Cys  Arg  Glu  Tyr  Cys  Gly  Val  Pro  Gly  Asp
Gly  Asp  Glu  Glu  Leu  Leu  Arg  Phe  Ser  Asn
```

Formula 24 (SEQ I.D. NO.:24)

```
ACC GTC GCC GCC TGC AAT CTC CCC ATA GTC
CGG GGC CCC TGC CGA GCC TTC ATC CAG CTC
TGG GCA TTT GAT GCT GTC AAG GGG AAG TGC
GTC CTC TTC CCC TAC GGG GGC TGC CAG GGC
AAC GGG AAC AAG TTC TAC TCA GAG AAG GAG
TGC AGA GAG TAC TGC GGT GTC CCT GGT GAT
GGT GAT GAG GAG CTG CTG CGC TTC TCC AAC
```

Figures 6, 7, 8, 9:
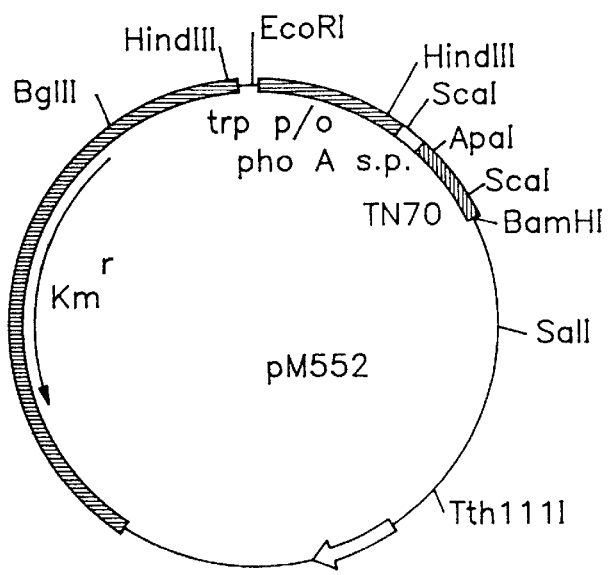
FIG. 6 is a map of a plasmid pM552.
FIG. 7 shows the nucleotide sequence of a HindIII primer (SEQ. I.D. NO.: 52).
FIG. 8 shows the nucleotide sequence of an AN68 primer (SEQ. I.D. NO.: 53).
FIG. 9 shows the nucleotide sequence of a pBR BamHI primer (SEQ. I.D. NO.: 54).

First, a HindIII primer (FIG. 7, SEQ. I.D. NO.: 52) and an AN68 primer (FIG. 8, SEQ. I.D. NO.: 53) were chemically synthesized. Using these oligonucleotides as sense primers and plasmid pM552 as a template, first PCR was carried out making use of GeneAmp Kit$^R$ (manufactured by Takara Shuzo Co., Ltd.) by repeating a total of 30 cycles, each cycle consisting of incubations at 94° C. for 1 minute, 55° C. for 2 minutes and 72° C. for 3 minutes. When a portion of the amplified product of the first PCR was subjected to 1.5% agarose gel electrophoresis, presence of a DNA fragment of interest having a size of about 130 bp was confirmed. The amplified product was purified by phenol treatment and ethanol precipitation and dissolved in TE buffer. Using this as a sense primer and plasmid pM552 as a template, second PCR was carried out in the same manner as the case of the first PCR. In this instance, a pBR BamHI primer (FIG. 9, SEQ. I.D. NO.: 54) was chemically synthesized and used as an antisense primer.

When a portion of the amplified product of the second PCR was subjected to 1.5% agarose gel electrophoresis, presence of a DNA fragment of interest having a size of about 350 bp was confirmed. The amplified product was purified by phenol treatment and ethanol precipitation, and the thus purified product was digested with restriction enzymes HindIII and BamHI to obtain a DNA fragment of about 300 bp.

Plasmid pM463 (op. cit.) was double-digested with restriction enzymes HindIII and BamHI to obtain a DNA fragment of about 3.3 kbp. Thereafter, this DNA fragment was ligated with the aforementioned DNA fragment of about 300 bp to obtain plasmid pM594 (SEQ. I.D. NOS.: 32 and 33).

[2] Preparation of plasmid pM710

A DNA fragment represented by the nucleotide sequence of FIG. 10 (fragment 1b, SEQ. I.D. NO.: 55) was designed by dividing it into 5 fragments and synthesized chemically in the same manner as described in Example 1, thereby obtaining a DNA fragment of about 150 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid (SEQ. I.D. NOS.: 32 and 33).

Confirmed partial nucleotide sequence of plasmid pM710 from its HindIII recognition site to BamHI recognition site and its corresponding amino acid sequence are shown in FIG. 11 (cf. SEQ. I.D. NOS.: 27 and 28 in the SEQUENCE LISTING).

[3] Preparation of plasmid pM776

A DNA fragment represented by the nucleotide sequence of FIG. 12 (fragment 2, (SEQ. I.D. NO.: 56) was designed by dividing it into 6 fragments and synthesized chemically in the same manner as described in Example 1, thereby obtaining a DNA fragment of about 200 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM776 (SEQ. I.D. NOS.: 36 and 37).

[4] Preparation of plasmid pM777

A DNA fragment represented by the nucleotide sequence of FIG. 13 (fragment 3, SEQ. I.D. NO.: 56) was designed by dividing it into 6 fragments and synthesized chemically in the same manner as described in Example 1, thereby obtaining a DNA fragment of about 150 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM777 (SEQ. I.D. NOS.: 38 and 39).

[5] Preparation of plasmid pM778

A DNA fragment represented by the nucleotide sequence of FIG. 14 (fragment 4, SEQ. I.D. NO.: 58) was designed by dividing it into 6 fragments and synthesized chemically in the same manner as described in Example 1, thereby obtaining a DNA fragment of about 150 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM778 (SEQ. I.D. NOS.: 40 and 41).

[6] Preparation of plasmid pM779

A DNA fragment represented by the nucleotide sequence of FIG. 15 (fragment 5, SEQ. I.D. NO.: 59) was designed by dividing it into 6 fragments and synthesized chemically in the same manner as described in Example 1, thereby obtaining a DNA fragment of about 160 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM779 (SEQ. I.D. NOS.: 42 and 43).

[7] Preparation of plasmid pM780

A DNA fragment represented by the nucleotide sequence of FIG. 16 (fragment 6, SEQ. I.D. NO.: 60) was designed by dividing it into 6 fragments and synthesized chemically in the same manner as described in Example 1, thereby obtaining a DNA fragment of about 160 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM780 (SEQ. I.D. NOS.: 44 and 45).

[8] Preparation of plasmid pM781

A DNA fragment represented by the nucleotide sequence of FIG. 17 (fragment 7, SEQ. I.D. NO.: 61) was designed by dividing it into 6 fragments and synthesized chemically in the same manner as described in Example 1, thereby obtaining a DNA fragment of about 160 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM781 (SEQ. I.D. NOS.: 46 and 47).

[9] Preparation of plasmid pM711

A DNA fragment represented by the nucleotide sequence of FIG. 18 (fragment 8, SEQ. I.D. NO.: 62) was designed by dividing it into 6 fragments and synthesized chemically in the same manner as described in Example 1, thereby obtaining a DNA fragment of about 150 bp. Separately from this, plasmid pM594 was double-digested with restriction enzymes HindIII and ApaI to obtain a DNA fragment of about 3.2 kbp. This was ligated with the chemically synthesized DNA fragment to obtain plasmid pM711 (SEQ. I.D. NOS.: 48 and 49).

[10] Comparison of extracellular secretion quantities

Using the plasmids obtained in [1] to [9], transformation of E. coli JE5505 was carried out in the same manner as described in Example 2 to obtain transformants JE5505 (pM594), JE5505 (pM710), JE5505 (pM776), JE5505 (pM777), JE5505 (pM778), JE5505 (pM779), JE5505 (pM780), JE5505 (pM781) and JE5505 (pM711). Each of these transformants was cultured and the resulting culture was centrifuged. The thus recovered culture supernatant was serially diluted with a 0.1% BSA/0.2M triethanolamine-HCl buffer (pH 7.8) to measure trypsin inhibitory activity by a procedure which will be described later. The results are shown below. Markedly high extracellular secretion quantities were found in the case of the plasmids containing the nucleotide sequence represented by x in comparison with the case of plasmid pM594. It was confirmed that the naturally extremely small extracellular secretion quantity of AN68 increases when the AN68 polypeptide is expressed in the form of a fusion protein with an amino acid sequence represented by X making use of the vector of the present invention.

| Transformant | Amino acid sequence encoded by x (nucleotide sequence of x) | Trypsin inhibitory activity* | Ratio |
|---|---|---|---|
| Experiment 1 | | | |
| JE5505 (pM594) | — | 4.5 | 1 |
| JE5505 (pM710) | formula 1 (formula 9) | 220 | 48.9 |
| Experiment 2 | | | |
| JE5505 (pM710) | formula 1 (formula 9) | 105 | 1 |
| JE5505 (pM776) | formula 2 (formula 10) | 75 | 0.7 |
| Experiment 3 | | | |
| JE5505 (pM710) | formula 1 (formula 9) | 188 | 1 |
| JE5505 (pM777) | formula 3 (formula 11) | 356 | 1.9 |
| JE5505 (pM778) | formula 4 (formula 12) | 891 | 4.7 |
| JE5505 (pM779) | formula 5 (formula 13) | 572 | 3.0 |
| JE5505 (pM789) | formula 6 (formula 14) | 737 | 3.9 |
| JE5505 (pM781) | formula 7 (formula 15) | 168 | 0.9 |
| Experiment 4 | | | |
| JE5505 (pM710) | formula 1 (formula 9) | 131 | 1 |
| JE5505 (pM711) | formula 8 (formula 16) | 81 | 0.6 |

*trypsin inhibitory activity in culture supernatant

[11] Comparison of intracellular expression quantities

Each of the transformants JE5505 (pM594) obtained in [1] and JE5505 (pM710) obtained in [2] was cultured. The resulting culture showed an optical density of 16 when measured at 550 nm using a spectrophotometer. A 6.3 $\mu$l portion of the culture was centrifuged to recover the resulting pellet. To this was added 10 $\mu$l of an electrophoresis buffer to a final concentration of 15% glycerol/0.0025% BPB/0.063M Tris-HCl (pH 6.8)/2% SDS/5% β-mercaptoethanol. Entire portion of the resulting mixture was subjected to SDS-polyacrylamide gel electrophoresis (to be referred to as "SDS-PAGE" hereinafter) in the following manner in accordance with the method of Laemmli (Laemmli U. K., Nature, vol.227, pp.680–685, 1970). Molecular weight markers of 43, 29, 18.4, 14.3 and 6.2 kD in size were purchased from BRL.

Figure 19:
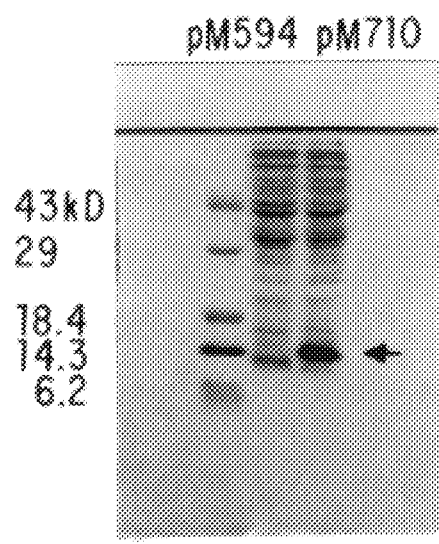
FIG. 19 shows the results of SDS-PAGE analysis of a protein obtained from cells of a transformant JE5505 (pM710) and a transformant JE5505 (pM594).

After completion of the electrophoresis, the resulting gel was stained with Coomassie Brilliant Blue R-250. As the result, distinctly large expression quantity was confirmed in JE5505 (pM710) in comparison with JE5505 (pM594) (see FIG. 19).

Example 4 Preparation of plasmid pM727

Plasmids were prepared in the following manner as vectors for use in the expression of polypeptide Q19K/Y46D, each containing a nucleotide sequence of j-x-y-z wherein j represents a nucleotide sequence which encodes the E. coli alkaline phosphatase signal sequence of the aforementioned formula 18, x represents the nucleotide sequence of the aforementioned formula 9, y represents a nucleotide sequence that encodes Met and z represents a nucleotide sequence which encodes polypeptide Q19K/Y46D.

[1] Construction of plasmid pM748

PCR was carried out twice using plasmid pM710 as a template under the same conditions as described in Example 3 [1]. In the first PCR, a chemically synthesized Y46D primer (FIG. 20, SEQ. I.D. NO.: 63) was used as a sense primer, and the aforementioned pBR BamHI primer as an antisense primer. When the thus amplified product was subjected to 1.5% agarose gel electrophoresis, a band of interest having about 120 bp in size was observed. Second PCR was carried out using this amplified product as an antisense primer, the aforementioned HindIII primer as a sense primer and plasmid pM710 as a template. When the amplified product was subjected to 1.5% agarose gel electrophoresis, a band of interest having a size of about 380 bp was observed. Thereafter, the amplified product was purified by phenol treatment and ethanol precipitation, and the purified product was inserted into plasmid pM463 in the same manner as described in Example 3 [1], thereby obtaining plasmid pM748.

[2] Construction of plasmid pM727

PCR was carried out twice using plasmid pM748 as a template under the same conditions as described in Example 3 [1]. In the first PCR, HindIII primer was used as a sense primer, and a chemically synthesized Q19K primer (FIG. 21, SEQ. I.D. NO.: 64) was used as an antisense primer. When the thus amplified product was subjected to 1.5% agarose gel electrophoresis, a band of interest having about 210 bp in size was observed. Second PCR was carried out using this amplified product as a sense primer, pBR BamHI primer as an antisense primer and plasmid pM748 as a template. When the thus amplified product was subjected to 1.5% agarose gel electrophoresis, a band of interest having a size of about 380 bp was observed. Thereafter, the amplified product was purified by phenol treatment and ethanol precipitation, and the purified product was inserted into plasmid pM463 in the same manner as described in Example 3 [1], thereby obtaining plasmid pM727.

Confirmed partial nucleotide sequence of plasmid pM727 from its HindIII recognition site to BamHI recognition site and its corresponding amino acid sequence are shown in FIG. 22 (cf. SEQ. I.D. NOS.: 30 and 31 in the SEQUENCE LISTING).

[3] Measurement of extracellular secretion quantity

A transformant JE5505 (pM727) was obtained by transforming *E. coli* JE5505 with the plasmid pM727 in the same manner as described in Example 2. The thus obtained transformant was cultured and the resulting culture was centrifuged. The thus recovered culture supernatant was serially diluted with a 0.1% BSA/0.2M triethanolamine-HCl buffer (pH 7.8) to measure trypsin inhibitory activity by a procedure which will be described later. As the result, a trypsin inhibitory activity of 117 U/ml was found in the culture supernatant, with a protein content of about 14 µg/ml when calculated from the specific activity. Since a definitely high extracellular secretion quantity was found in comparison with a case in which the vector of the present invention was not used, it was confirmed that the naturally extremely small extracellular secretion quantity of Q19K/Y46D increases when the Q19K/Y46D polypeptide is expressed in the form of a fusion protein with an amino acid sequence represented by X.

Example 5 Preparation of plasmid pM765

Plasmid pM765 was prepared in the following manner as a vector for use in the expression of polypeptide R11S/Q19K/Y46D, which contains a nucleotide sequence of j-x-y-z wherein j represents a nucleotide sequence which encodes the *E. coli* alkaline phosphatase signal sequence of the aforementioned formula 18, x represents the nucleotide sequence of the aforementioned formula 9, y represents a nucleotide sequence that encodes Met and z represents a nucleotide sequence which encodes polypeptide R11S/Q19K/Y46D.

[1] Construction of plasmid pM765

PCR was carried out twice using plasmid pM727 as a template under the same conditions as described in Example 3 [1]. In the first PCR, HindIII primer was used as a sense primer, and a chemically synthesized R11S primer (FIG. 23, SEQ. I.D. NO.: 65) as an antisense primer. When the thus amplified product was subjected to 1.5% agarose gel electrophoresis, a band of interest having about 180 bp in size was observed. Second PCR was carried out using this amplified product as a sense primer, pBR BamHI primer as an antisense primer and plasmid pM727 as a template. When the amplified product of the second PCR was subjected to 1.5% agarose gel electrophoresis, a band of interest having a size of about 380 bp was observed. Thereafter, the amplified product was purified by phenol treatment and ethanol precipitation, and the purified product was inserted into plasmid pM463 in the same manner as described in Example 3 [1], thereby obtaining expression plasmid pM765.

Confirmed partial nucleotide sequence of plasmid pM765 from its HindIII recognition site to BamHI recognition site and its corresponding amino acid sequence are shown in FIG. 24 (cf. SEQ. I.D. NOS.: 32 and 33 in the SEQUENCE LISTING).

[2] Measurement of extracellular secretion quantity

A transformant JE5505 (pM765) was obtained by transforming *E. coli* JE5505 with the plasmid pM765 in the same manner as described in Example 2. The thus obtained transformant was cultured and the resulting culture was centrifuged. The thus recovered culture supernatant was serially diluted with a 0.1% BSA/0.2M triethanolamine-HCl buffer (pH 7.8) to measure trypsin inhibitory activity by a procedure which will be described later. As the result, a trypsin inhibitory activity of 460 U/ml was found in the culture supernatant, with a protein content of about 75 µg/ml when calculated from the specific activity. Since a definitely high extracellular secretion quantity was found in comparison with a case in which the vector of the present invention was not used, it was confirmed that the extracellular secretion quantity of polypeptide R11S/Q19K/Y46D increases when the polypeptide is expressed in the form of a fusion protein with an amino acid sequence represented by X.

Example 6 Production of polypeptide R11S/O19K/Y46D making use of plasmid pM765

[1] Using plasmid pM765, transformation of *E. coli* JE5505 was carried out in the same manner as described in Example 2 to obtain an *E. coli* transformant JE5505 (pM765). This strain has been deposited by the present inventors on Apr. 28, 1993, in National Institute of Bioscience and Human Technology, Agency of Industrial Science and Technology, Ministry of International Trade and Industry, 1–3, Higashi 1-chome, Tsukuba-shi, Ibaraki, and has been assigned the designation as FERM BP-4285 which was subsequently cultured. The resulting culture was concentrated using Benchmark GX (0.2 µm in pore size, manufactured by Membrex) and then centrifuged for 20 minutes at about 10,000×g and at 4° C. to recover the transformant cells.

[2] The cells thus recovered in the above step [1] were suspended in solution for disruption (0.5% Triton X-100 and 10 mM EDTA) and disrupted using Mini Labo (manufactured by Rannie) under a pressure of 800 bar. The resulting suspension was centrifuged for 20 minutes at about 10,000×g and at 4° C. to recover the pellet. The thus recovered pellet was suspended in the solution for disruption and again centrifuged for 20 minutes at about 10,000×g and at 4° C. This suspension/centrifugation step was repeated two more times. The thus finally recovered pellet was suspended in a solubilization buffer (5M guanidine hydrochloride, 0.005% Tween 80, 50 mM Tris-HCl (pH 8.0), 5 mM EDTA, 2 mM reduced glutathione, 0.02 mM oxidized glutathione) to which was further added 2-mercaptoethanol to a final concentration of 50 mM. After overnight stirring of the mixture at 4° C., the resulting solution was concentrated using an ultrafiltration membrane (YM-5, manufactured by Grace Japan) and then filtered through a 0.44 μm filter.

The thus concentrated filtrate was applied to a column (5 cmø×95 cm) packed with Sephacryl S-100 HR (manufactured by Pharmacia) which has been equilibrated in advance with the aforementioned solubilization buffer. Using the solubilization buffer as an elution buffer, gel filtration was carried out at a flow rate of 3.5 ml/min, while monitoring changes in the absorbance at 280 nm as an index of the protein content. The eluate was collected in 30 ml portions, and a small portion of each of the thus collected fractions was subjected to SDS-PAGE using PAGEL$^R$ (SPU-15S, manufactured by ATTO Corp.) in accordance with the manufacturer's recommendations. The resulting gels were stained with Coomassie Brilliant Blue to select a fraction containing a large quantity of a polypeptide having intended molecular weight. Protein content in the thus selected fraction was adjusted to approximately 0.5 mg/ml with the solubilization buffer and used as a sample for the refolding treatment.

[3] The sample for refolding treatment use obtained in the above step [2] was dialyzed twice against about 15 volumes of the solubilization solution from which guanidine hydrochloride has been eliminated and then three times against about 15 volumes of distilled water. Thereafter, the thus dialyzed sample was adjusted to pH 2 with hydrochloric acid and subjected to purification in the following manner.

[4] The sample obtained by the refolding treatment in the above step [3] was applied to a PLRP-S column (25 mmø× 150 mm, manufactured by Polymer Laboratories) which has been equilibrated in advance with 0.1% TFA solution. Elution of the adsorbed sample was carried out using 0.1% TFA/acetonitrile solution at a flow rate of 5 ml/min by linear acetonitrile density gradient (0 to 70% acetonitrile/0.1% TFA solution/30 minutes, 70 to 100% acetonitrile/0.1% TFA solution/3 minutes). Changes in the absorbance at 280 nm were monitored and the eluate was collected in 5 ml portions. Trypsin inhibitory activity in each fraction was measured by a procedure which will be described later, and fractions having the inhibitory activity were pooled, freezedried and then dissolved in 70% formic acid to a concentration of about 100 μM. To this was added cyanogen bromide in 2,000 times higher mol concentration ratio. After 24 hours of standing at 25° C. in the dark, the resulting solution was diluted with the same volume of distilled water.

[5] A column packed with SP-Toyopearl (30 mmø×150 mm, manufactured by Tosoh Corp.) was equilibrated with 10% formic acid solution to carry out a cation exchange chromatography in the following manner using an FPLC system (op. cit.). That is, the sample obtained in the above step [4] was applied to the thus equilibrated SP-Toyopearl. Elution of the adsorbed sample was carried out using NaCl/10% formic acid solution at a flow rate of 8 ml/min by linear NaCl density gradient (0 to 1.2M NaCl/10% formic acid solution/100 minutes). Changes in the absorbance at 280 nm were monitored and the eluate was collected in 32 ml portions. Trypsin inhibitory activity in each fraction was measured by a procedure which will be described later. Active fractions thus obtained were used in the following reverse phase chromatography.

[6] Active fractions obtained in the above step [5] were pooled and applied to a PLRP-S column (25 mmø×150 mm, manufactured by Polymer Laboratories) which has been equilibrated in advance with 0.1% TFA solution. Elution of the adsorbed sample was carried out using 0.1% TFA/acetonitrile solution at a flow rate of 10 ml/min by linear acetonitrile density gradient (0 to 70% acetonitrile/0.1% TFA solution/15 minutes, 70 to 100% acetonitrile/0.1% TFA solution/3 minutes). Changes in the absorbance at 280 nm were monitored and the eluate of each peak was collected. Trypsin inhibitory activity in each fraction was measured by a procedure which will be described later. The thus obtained active fraction was freezedried to obtain a purified product.

[7] The purified product obtained in the above step [6] was subjected to SDS-PAGE using PAGEL$^R$ (op. cit.). When the resulting gel was subjected to silver staining, a single band was observed.

[8] Analysis of amino acid sequence

The purified polypeptide obtained in the above step [6] was dissolved in 50% acetic acid and subjected to an amino acid sequence analyzer (Model 477A Protein Sequencing System-120A PTH Analyzer, manufactured by Applied Biosystems). PTH amino acids were detected by their UV absorption at 270 nm to measure corresponding retention times, and each amino acid was identified based on the retention times of standard PTH amino acids (manufactured by Applied Biosystems) measured by the same procedure. As the result, purification of the protein of interest, R11S/Q19K/Y46D, was confirmed.

Example 7 Production of polypeptide O19K/Y46D making use of plasmid pM727

[1] A transformant JE5505 (pM727) was obtained by transforming *E. coli* JE5505 with the plasmid pM727 in the same manner as described in Example 2. After culturing the thus obtained transformant, the resulting culture supernatant was recovered, adjusted to pH 2 with 6N HCl and then filtered through a 1.0 μm filter (manufactured by Pall Trinity Micro Corp.). The resulting filtrate was further filtered using a CN cartridge (0.22 μm in pore size, manufactured by Millipore Corp.).

[2] The filtrate obtained in the above step [1] was applied to SP-Toyopearl (550C, manufactured by Tosoh Corp.) which has been equilibrated in advance with 50 mM glycine-HCl buffer (pH 2.0). After washing the resulting resin with 50 mM ammonium formate (pH 3.0), elution was effected using 50 mM ammonium formate (pH 5.0) while monitoring absorption of the eluate at a wave length of 280 nm. Trypsin inhibitory activity in each fraction was measured by a procedure which will be described later. The thus obtained active fraction was concentrated using an ultrafiltration membrane (Filtron, manufactured by Fuji Filter; molecular weight cutoff of 3,000) and then filtered through a 0.22 μm filter to remove precipitated materials. The resulting filtrate was recovered and used in the following gel filtration.

[3] The filtrate obtained in the above step [2] was applied to a Superdex 75 column (26 mmø×600 mm, manufactured by Pharmacia) which has been equilibrated in advance with 50 mM ammonium formate (pH 5.0). Elution of the adsorbed sample was carried out using 50 mM ammonium formate (pH 5.0) at a flow rate of 2 ml/min. Changes in the absorbance at 280 nm were monitored and the eluate was collected in 6 ml portions. Trypsin inhibitory activity in each fraction was measured by a procedure which will be described later. The thus obtained active fractions were pooled and freeze-dried.

[4] The freeze-dried product obtained in the above step [3] was subjected to cyanogen bromide cleavage and purification in accordance with the procedures [4], [5] and [6] of Example 6. When the thus purified product was subjected to SDS-PAGE by the procedure [7] of Example 6, a single band was observed. Amino acid analysis of the purified product in accordance with the procedure [8] of Example 6 revealed that the product was the protein of interest, Q19K/Y46D.

Measurement of trypsin inhibitory activity

A culture was subjected to centrifugation, and the resulting culture supernatant was serially diluted with a 0.1% BSA/0.2M triethanolamine hydrochloride buffer (pH 7.8) to be used as samples for the measurement of bovine trypsin inhibitory activity. Bovine trypsin inhibitory activity in these samples was measured in the following manner using a synthetic substrate S-2444 (manufactured by Kabi Diagnostica AB.), in accordance with the method of Kassell (Kassell B. et al., *Methods in Enzyrnol.*, vol.19, pp.844–852, 1970).

Firstly, bovine trypsin (Type XIII, manufactured by Sigma Chemical Co.) was dissolved in 0.001M HCl to a concentration of 13,600 BAEEU/ml and then diluted with the 0.1% BSA/0.2M triethanolamine hydrochloride buffer (pH 7.8) to prepare a trypsin solution of 0.6 BAEEU/ml. Separately from this, the synthetic substrate S-2444 was dissolved in distilled water to prepare 2 mM S-2444 solution.

Next, a 100 $\mu$l portion of the above sample for use in bovine trypsin inhibitory activity measurement or a control solution was mixed with 100 $\mu$l of the bovine trypsin solution. After 10 minutes of preincubation at 37° C., the reaction was started by adding 50 $\mu$l of the S-2444 solution. After 20 minutes of incubation at 37° C., the reaction was terminated by adding 50 $\mu$l of 50% acetic acid to measure absorption of the reaction mixture at a wave length of 405 nm using a spectrophotometer. In order to eliminate absorption of components in each solution used in the reaction, a blank solution was prepared by adding 50 $\mu$l of 50% acetic acid to 100 $\mu$l of the bovine trypsin solution and then adding 100 $\mu$l of the sample to be measured or the control solution and 50 $\mu$l of the S-2444 solution to the mixture.

Thus, as has been described in the foregoing, it is apparent that, in planning protein production making use of recombinant DNA techniques, expression of a protein of interest and/or its secretion from host cells into the extracellular milieu can be increased by expressing the protein of interest in the form of a fusion protein with a specified polypeptide using the inventive vector which contains the DNA fragment of the present invention.

In consequence, the present invention is effective in increasing production yield of a protein of interest when the protein is produced by means of recombinant DNA techniques and also renders possible extracellular expression of a protein which is hardly expressed extracellularly as its nature.

What is claimed is:

1. An isolated DNA molecule comprising a nucleotide sequence encoding a polypeptide that does not occur in nature which comprises an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16.

2. An isolated DNA molecule comprising a nucleotide sequence encoding a polypeptide comprising an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16, wherein, when said polypeptide is a fusion peptide having an amino acid sequence selected from the group consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16 fused to a protein of interest, said polypeptide assists a signal sequence to secrete said fusion protein into a culture medium by a bacterial host cell expressing said isolated DNA molecule.

3. The isolated DNA molecule of claim 2, wherein said polypeptide is secreted into said culture medium in an amount greater than 50 µg/ml.

4. An isolated DNA molecule comprising a nucleotide sequence encoding a polypeptide comprising an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16, wherein, when said polypeptide is a fusion peptide having an amino acid sequence selected from the group consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16 fused to the peptide PSTI, said polypeptide is secreted by a signal sequence in an amount greater than 50 µg/ml into a culture medium by *E. coli* expressing said isolated DNA molecule.

5. The DNA molecule according to claim 1, wherein said nucleotide sequence is selected from the group consisting of SEQ. I.D. NO. 1, SEQ. I.D. NO. 3, SEQ. I.D. NO. 5, SEQ. I.D. NO. 7, SEQ. I.D. NO. 9, SEQ. I.D. NO. 11, SEQ. I.D. NO. 13 and SEQ. I.D. NO. 15.

6. An isolated DNA molecule comprising a nucleotide sequence encoding a signal peptide and at least a nucleotide sequence encoding a polypeptide that does not occur in nature which comprises an amino acid sequence seqlected from the group of amino acid sqeuences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16.

7. An isolated DNA molecule which comprises a nucleotide sequence represented by the formula j-x, wherein j is a nucleotide sequence which encodes a signal peptide; and x is a nucleotide sequence encoding an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16.

8. A recombinant DNA vector which comprises at least one DNA molecule according to claim 11.

9. A recombinant DNA vector which comprises at least DNA molecule sequence according to claim 5.

10. A recombinant DNA vector which comprises at least one DNA molecule according to claim 7.

11. A recombinant DNA vector which comprises a nucleotide sequence represented by the formula j-x-y, wherein j is a nucleotide sequence which encodes a signal peptide;

x is a nucleotide sequence encoding an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16; and y is a nucleotide sequence encoding an amino acid or amino acid sequence which is recognized and cleaved by an enzyme and/or a chemical compound.

12. A vector which comprises a nucleotide sequence represented by j-x-z, wherein j is a nucleotide sequence which encodes a signal peptide;

x is a nucleotide sequence which encodes an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16; and z is a nucleotide sequence which encodes a protein of interest.

13. A recombinant DNA vector which comprises a nucleotide sequence represented by the formula j-x-y-z, wherein j is a nucleotide sequence which encodes a signal peptide;

x is a nucleotide sequence encoding an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16;

y is a nucleotide sequence encoding an amino acid or amino acid sequence which is recognized and cleaved by an enzyme and/or a chemical compound; and z is a nucleotide sequence which encodes an amino acid sequence of a protein of interest.

14. A vector according to any one of claims 8 to 13, wherein said vector further contains a promoter selected from the group consisting of a trp promoter, a tac promoter and a lac promoter.

15. A cell transformed with a vector according to any one of claims 8 to 13.

16. A cell transformed with a vector according to claim 14.

17. A transformed cell according to claim 15, wherein said cell is a cell of *Eschericia coli, Bacillus subtilis* or a yeast.

18. A transformed cell according to claim 16, wherein said cell is a cell of *Eschericia coli, Bacillus subtilis* or a yeast.

19. A process for producing a protein of interest which comprises:

i) transforming a host cell with a vector according to claim 8 or 9 to obtain a transformed host cell;

ii) culturing said transformed host cells so as to obtain expression of said DNA encoding said polypeptide and its secretion into a medium used for culturing said transformed host cells; and iii) recovering the protein of interest from said medium or from said host cells.

20. A process according to claim 19, wherein said protein of interest is secreted in an amount greater than 50 µg/ml.

21. A process for producing a protein of interest comprising:

i) culturing a cell transformed with a vector according to claim 2 or 3, thereby effecting expression of a protein having an amino acid sequence represented by the formula J-X-Z or J-X-Y-Z, wherein J is a signal peptide;

X is an amino acid sequence selected from the group of amino acid sequences consisting of SEQ. I.D. NO. 2, SEQ. I.D. NO. 4, SEQ. I.D. NO. 6, SEQ. I.D. NO. 8, SEQ. I.D. NO. 10, SEQ. I.D. NO. 12, SEQ. I.D. NO. 14 and SEQ. I.D. NO. 16;

Y is selected from the group consisting of a methionine residue, a lysine residue, an arginine residue and the amino acid sequence isoleucine-glutamic acid-qlycine-arginine; and Z is a protein of interest.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..33
        ( D ) OTHER INFORMATION: /label=oligonucleotide
            / note= "Formula 9"

( i x ) FEATURE:
        ( A ) NAME/KEY: CDS
        ( B ) LOCATION: 1..33
        ( D ) OTHER INFORMATION: /product="peptide X1, Formula 1"

( x i ) SEQUENCE DESCRIPTION: SEQ ID NO:1:

```
GCT  GTG  CTA  CCG  CAA  GAA  GAA  GAA  GGC  TCG  GGT              3 3
Ala  Val  Leu  Pro  Gln  Glu  Glu  Glu  Gly  Ser  Gly
 1              5                              1 0
```

( 2 ) INFORMATION FOR SEQ ID NO:2:

( i ) SEQUENCE CHARACTERISTICS:
        ( A ) LENGTH: 11 amino acids (B) TYPE: amino acid
(D) TOPOLOGY: linear (i i) MOLECULE TYPE: protein (x i) SEQUENCE DESCRIPTION: SEQ ID NO:2:

```
Ala  Val  Leu  Pro  Gln  Glu  Glu  Glu  Gly  Ser  Gly
 1              5                        10
```

(2) INFORMATION FOR SEQ ID NO:3:

(i) SEQUENCE CHARACTERISTICS:
      (A) LENGTH: 78 base pairs
      (B) TYPE: nucleic acid
      (C) STRANDEDNESS: single
      (D) TOPOLOGY: linear (i i) MOLECULE TYPE: DNA (i x) FEATURE:
      (A) NAME/KEY: -
      (B) LOCATION: 1..78
      (D) OTHER INFORMATION: /label=oligonucleotide
          / note= "Formula 10"

(i x) FEATURE:
      (A) NAME/KEY: CDS
      (B) LOCATION: 1..78
      (D) OTHER INFORMATION: /product="peptide X2, Formula 2"

(x i) SEQUENCE DESCRIPTION: SEQ ID NO:3:

```
GCT  GTG  CTA  CCC  CAA  GAA  GAG  GAA  GGA  TCA  GGG  GGT  GGG  CAA  CTG  GTA    48
Ala  Val  Leu  Pro  Gln  Glu  Glu  Glu  Gly  Ser  Gly  Gly  Gly  Gln  Leu  Val
 1              5                        10                       15

ACT  GAA  GTC  ACC  AAG  AAA  GAA  GAC  TCG  GGT                                  78
Thr  Glu  Val  Thr  Lys  Lys  Glu  Asp  Ser  Gly
              20                        25
```

(2) INFORMATION FOR SEQ ID NO:4:

(i) SEQUENCE CHARACTERISTICS:
      (A) LENGTH: 26 amino acids
      (B) TYPE: amino acid
      (D) TOPOLOGY: linear (i i) MOLECULE TYPE: protein (x i) SEQUENCE DESCRIPTION: SEQ ID NO:4:

```
Ala  Val  Leu  Pro  Gln  Glu  Glu  Glu  Gly  Ser  Gly  Gly  Gly  Gln  Leu  Val
 1              5                        10                       15

Thr  Glu  Val  Thr  Lys  Lys  Glu  Asp  Ser  Gly
              20                        25
```

(2) INFORMATION FOR SEQ ID NO:5:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (i i) MOLECULE TYPE: DNA (i x) FEATURE:
      (A) NAME/KEY: -
      (B) LOCATION: 1..33
      (D) OTHER INFORMATION: /label=oligonucleotide
          / note= "Formula 11"

(i x) FEATURE:
      (A) NAME/KEY: CDS
      (B) LOCATION: 1..33

(D) OTHER INFORMATION: /product="peptide X3, Formula 3"

(xi) SEQUENCE DESCRIPTION: SEQ ID NO:5:

```
GCT GTG CTA GAT CAA GAA GAA GAA GGC TCG GGT                          33
Ala Val Leu Asp Gln Glu Glu Glu Gly Ser Gly
 1               5                   10
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Val Leu Asp Gln Glu Glu Glu Gly Ser Gly
 1               5                   10
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /label=oligonucleotide
            /note= "Formula 12"

(ix) FEATURE:
        (A) NAME/KEY: CDS
        (B) LOCATION: 1..33
        (D) OTHER INFORMATION: /product="peptide X4, Formula 4"

(xi) SEQUENCE DESCRIPTION: SEQ ID NO:7:

```
GCT GTG CTA CCG CAA GAA GAA GAA GGC GAT GGT                          33
Ala Val Leu Pro Gln Glu Glu Glu Gly Asp Gly
 1               5                   10
```

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:8:

```
Ala Val Leu Pro Gln Glu Glu Glu Gly Asp Gly
 1               5                   10
```

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36

( D ) OTHER INFORMATION: /label=oligonucleotide
/ note= "Formula 13"

( i x ) FEATURE:
( A ) NAME/KEY: CDS
( B ) LOCATION: 1..36
( D ) OTHER INFORMATION: /product="peptide X5, Formula 5"

( x i ) SEQUENCE DESCRIPTION: SEQ ID NO:9:

| GCT | GTG | CTA | CCG | CAA | GAA | GAA | GAA | GGC | TCG | GGT | GAT | 36 |
|---|---|---|---|---|---|---|---|---|---|---|---|---|
| Ala | Val | Leu | Pro | Gln | Glu | Glu | Glu | Gly | Ser | Gly | Asp | |
| 1 | | | | 5 | | | | | 10 | | | |

( 2 ) INFORMATION FOR SEQ ID NO:10:

( i ) SEQUENCE CHARACTERISTICS:
( A ) LENGTH: 12 amino acids
( B ) TYPE: amino acid
( D ) TOPOLOGY: linear ( i i ) MOLECULE TYPE: protein ( x i ) SEQUENCE DESCRIPTION: SEQ ID NO:10:

Ala Val Leu Pro Gln Glu Glu Glu Gly Ser Gly Asp
1               5                       10

( 2 ) INFORMATION FOR SEQ ID NO:11:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: -
( B ) LOCATION: 1..39
( D ) OTHER INFORMATION: /label=oligonucleotide
/ note= "Formula 14"

( i x ) FEATURE:
( A ) NAME/KEY: CDS
( B ) LOCATION: 1..39
( D ) OTHER INFORMATION: /product="peptide X6, Formula 6"

( x i ) SEQUENCE DESCRIPTION: SEQ ID NO:11:

| GCT | GTG | CTA | CCG | CAA | GAA | GAA | GAA | GGC | TCG | GGT | GAT | GAT | 39 |
|---|---|---|---|---|---|---|---|---|---|---|---|---|---|
| Ala | Val | Leu | Pro | Gln | Glu | Glu | Glu | Gly | Ser | Gly | Asp | Asp | |
| 1 | | | | 5 | | | | | 10 | | | | |

( 2 ) INFORMATION FOR SEQ ID NO:12:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( x i ) SEQUENCE DESCRIPTION: SEQ ID NO:12:

Ala Val Leu Pro Gln Glu Glu Glu Gly Ser Gly Asp Asp
1               5                       10

( 2 ) INFORMATION FOR SEQ ID NO:13:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear (i i) MOLECULE TYPE: DNA (i x) FEATURE:
    (A) NAME/KEY: -
    (B) LOCATION: 1..42
    (D) OTHER INFORMATION: /label=oligonucleotide
        / note= "Formula 15"

(i x) FEATURE:
    (A) NAME/KEY: CDS
    (B) LOCATION: 1..42
    (D) OTHER INFORMATION: /product="peptide X7, Formula 7"

(x i) SEQUENCE DESCRIPTION: SEQ ID NO:13:

```
GCT  GTG  CTA  CCG  CAA  GAA  GAA  GAA  GGC  TCG  GGT  GAT  GAT  GAT      42
Ala  Val  Leu  Pro  Gln  Glu  Glu  Glu  Gly  Ser  Gly  Asp  Asp  Asp
 1              5                        10
```

(2) INFORMATION FOR SEQ ID NO:14:

(i) SEQUENCE CHARACTERISTICS:
        (A) LENGTH: 14 amino acids
        (B) TYPE: amino acid
        (D) TOPOLOGY: linear (i i) MOLECULE TYPE: protein (x i) SEQUENCE DESCRIPTION: SEQ ID NO:14:

```
Ala  Val  Leu  Pro  Gln  Glu  Glu  Glu  Gly  Ser  Gly  Asp  Asp  Asp
 1              5                        10
```

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: -
        (B) LOCATION: 1..33
        (D) OTHER INFORMATION: /label=oligonucleotide
            / note= "Formula 16"

(i x) FEATURE:
        (A) NAME/KEY: CDS
        (B) LOCATION: 1..33
        (D) OTHER INFORMATION: /product="peptide X8, Formula 8"

(x i) SEQUENCE DESCRIPTION: SEQ ID NO:15:

```
GCT  GAC  GAC  CCG  CAA  GAA  GAA  GAA  GGC  TCG  GGT                    33
Ala  Asp  Asp  Pro  Gln  Glu  Glu  Glu  Gly  Ser  Gly
 1              5                        10
```

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:16:

```
Ala  Asp  Asp  Pro  Gln  Glu  Glu  Glu  Gly  Ser  Gly
 1              5                        10
```

(2) INFORMATION FOR SEQ ID NO:17:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: -
    ( B ) LOCATION: 1..63
    ( D ) OTHER INFORMATION: /label=oligonucleotide
        / note= "j, Formula 17, encoding E. coli alkaline
        phosphatase signal peptide"

( i x ) FEATURE:
    ( A ) NAME/KEY: CDS
    ( B ) LOCATION: 1..63
    ( D ) OTHER INFORMATION: /product="J, Formula 18, E. coli
        alkaline phosphatase signal peptide"

( x i ) SEQUENCE DESCRIPTION: SEQ ID NO:17:

```
ATG  AAA  CAA  AGT  ACT  ATT  GCA  CTG  GCA  CTC  TTA  CCG  TTA  CTG  TTT  ACC        48
Met  Lys  Gln  Ser  Thr  Ile  Ala  Leu  Ala  Leu  Leu  Pro  Leu  Leu  Phe  Thr
 1                    5                    10                   15

CCT  GTG  ACA  AAG  GCC                                                                63
Pro  Val  Thr  Lys  Ala
               20
```

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Lys  Gln  Ser  Thr  Ile  Ala  Leu  Ala  Leu  Leu  Pro  Leu  Leu  Phe  Thr
 1                    5                    10                   15

Pro  Val  Thr  Lys  Ala
               20
```

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..4
        ( D ) OTHER INFORMATION: /label=peptide
            / note= "Y, Factor Xa cleavage site"

( x i ) SEQUENCE DESCRIPTION: SEQ ID NO:19:

```
Ile  Glu  Gly  Arg
 1
```

( 2 ) INFORMATION FOR SEQ ID NO:20:

( i ) SEQUENCE CHARACTERISTICS:
        ( A ) LENGTH: 56 amino acids ( B ) TYPE: amino acid
            ( D ) TOPOLOGY: linear ( i i ) MOLECULE TYPE: peptide ( v ) FRAGMENT TYPE: internal ( i x ) FEATURE:
            ( A ) NAME/KEY: Peptide
            ( B ) LOCATION: 1..56
            ( D ) OTHER INFORMATION: /label=peptide
                    / note= "Formula 19, PSTI"

( x i ) SEQUENCE DESCRIPTION: SEQ ID NO:20:

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

( 2 ) INFORMATION FOR SEQ ID NO:21:

( i ) SEQUENCE CHARACTERISTICS:
            ( A ) LENGTH: 68 amino acids
            ( B ) TYPE: amino acid
            ( D ) TOPOLOGY: linear ( i i ) MOLECULE TYPE: peptide ( v ) FRAGMENT TYPE: internal ( i x ) FEATURE:
            ( A ) NAME/KEY: Peptide
            ( B ) LOCATION: 1..68
            ( D ) OTHER INFORMATION: /label=peptide
                    / note= "Formula 20, AN68"

( x i ) SEQUENCE DESCRIPTION: SEQ ID NO:21:

Ala Ala Cys Asn Leu Pro Ile Val Arg Gly Pro Cys Arg Ala Phe Ile
1               5                   10                  15

Gln Leu Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro Gly Asp Gly Asp Glu Glu Leu Leu
        50                  55                  60

Arg Phe Ser Asn
65

( 2 ) INFORMATION FOR SEQ ID NO:22:

( i ) SEQUENCE CHARACTERISTICS:
            ( A ) LENGTH: 68 amino acids
            ( B ) TYPE: amino acid
            ( D ) TOPOLOGY: linear ( i i ) MOLECULE TYPE: peptide ( v ) FRAGMENT TYPE: internal ( i x ) FEATURE:
            ( A ) NAME/KEY: Peptide
            ( B ) LOCATION: 1..68
            ( D ) OTHER INFORMATION: /label=peptide
                    / note= "Formula 21, Q19K/Y46D"

( x i ) SEQUENCE DESCRIPTION: SEQ ID NO:22:

| Ala | Ala | Cys | Asn | Leu | Pro | Ile | Val | Arg | Gly | Pro | Cys | Arg | Ala | Phe | Ile |
|---|---|---|---|---|---|---|---|---|---|---|---|---|---|---|---|
| 1 | | | | 5 | | | | | 10 | | | | | 15 | |

| Lys | Leu | Trp | Ala | Phe | Asp | Ala | Val | Lys | Gly | Lys | Cys | Val | Leu | Phe | Pro |
|---|---|---|---|---|---|---|---|---|---|---|---|---|---|---|---|
| | | | 20 | | | | | 25 | | | | | 30 | | |

| Tyr | Gly | Gly | Cys | Gln | Gly | Asn | Gly | Asn | Lys | Phe | Asp | Ser | Glu | Lys | Glu |
|---|---|---|---|---|---|---|---|---|---|---|---|---|---|---|---|
| | | 35 | | | | | 40 | | | | | 45 | | | |

| Cys | Arg | Glu | Tyr | Cys | Gly | Val | Pro | Gly | Asp | Gly | Asp | Glu | Glu | Leu | Leu |
|---|---|---|---|---|---|---|---|---|---|---|---|---|---|---|---|
| | 50 | | | | | 55 | | | | | 60 | | | | |

| Arg | Phe | Ser | Asn |
|---|---|---|---|
| 65 | | | |

( 2 ) INFORMATION FOR SEQ ID NO:23:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..68
        ( D ) OTHER INFORMATION: /label=peptide
                / note= "Formula 22, R11S/Q19K/Y46D"

( x i ) SEQUENCE DESCRIPTION: SEQ ID NO:23:

| Ala | Ala | Cys | Asn | Leu | Pro | Ile | Val | Ser | Gly | Pro | Cys | Arg | Ala | Phe | Ile |
|---|---|---|---|---|---|---|---|---|---|---|---|---|---|---|---|
| 1 | | | | 5 | | | | | 10 | | | | | 15 | |

| Lys | Leu | Trp | Ala | Phe | Asp | Ala | Val | Lys | Gly | Lys | Cys | Val | Leu | Phe | Pro |
|---|---|---|---|---|---|---|---|---|---|---|---|---|---|---|---|
| | | | 20 | | | | | 25 | | | | | 30 | | |

| Tyr | Gly | Gly | Cys | Gln | Gly | Asn | Gly | Asn | Lys | Phe | Asp | Ser | Glu | Lys | Glu |
|---|---|---|---|---|---|---|---|---|---|---|---|---|---|---|---|
| | | 35 | | | | | 40 | | | | | 45 | | | |

| Cys | Arg | Glu | Tyr | Cys | Gly | Val | Pro | Gly | Asp | Gly | Asp | Glu | Glu | Leu | Leu |
|---|---|---|---|---|---|---|---|---|---|---|---|---|---|---|---|
| | 50 | | | | | 55 | | | | | 60 | | | | |

| Arg | Phe | Ser | Asn |
|---|---|---|---|
| 65 | | | |

( 2 ) INFORMATION FOR SEQ ID NO:24:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..210
        ( D ) OTHER INFORMATION: /label=polynucleotide
                / note= "Formula 24, encodes a portion of E. coli
                alkaline phosphatase downstream from the signal
                peptide."

( i x ) FEATURE:
        ( A ) NAME/KEY: CDS
        ( B ) LOCATION: 1..210
        ( D ) OTHER INFORMATION: /product="Formula 23, a portion of
                E. coli alkaline phosphatase"

( x i ) SEQUENCE DESCRIPTION: SEQ ID NO:24:

ACC GTC GCC GCC TGC AAT CTC CCC ATA GTC CGG GGC CCC TGC CGA GCC     48

```
Thr  Val  Ala  Ala  Cys  Asn  Leu  Pro  Ile  Val  Arg  Gly  Pro  Cys  Arg  Ala
 1                   5                   10                       15

TTC  ATC  CAG  CTC  TGG  GCA  TTT  GAT  GCT  GTC  AAG  GGG  AAG  TGC  GTC  CTC       96
Phe  Ile  Gln  Leu  Trp  Ala  Phe  Asp  Ala  Val  Lys  Gly  Lys  Cys  Val  Leu
               20                   25                        30

TTC  CCC  TAC  GGG  GGC  TGC  CAG  GGC  AAC  GGG  AAC  AAG  TTC  TAC  TCA  GAG      144
Phe  Pro  Tyr  Gly  Gly  Cys  Gln  Gly  Asn  Gly  Asn  Lys  Phe  Tyr  Ser  Glu
               35                        40                   45

AAG  GAG  TGC  AGA  GAG  TAC  TGC  GGT  GTC  CCT  GGT  GAT  GGT  GAT  GAG  GAG      192
Lys  Glu  Cys  Arg  Glu  Tyr  Cys  Gly  Val  Pro  Gly  Asp  Gly  Asp  Glu  Glu
          50                    55                        60

CTG  CTG  CGC  TTC  TCC  AAC                                                        210
Leu  Leu  Arg  Phe  Ser  Asn
 65                       70
```

( 2 ) INFORMATION FOR SEQ ID NO:25:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Thr  Val  Ala  Ala  Cys  Asn  Leu  Pro  Ile  Val  Arg  Gly  Pro  Cys  Arg  Ala
 1                   5                   10                       15

Phe  Ile  Gln  Leu  Trp  Ala  Phe  Asp  Ala  Val  Lys  Gly  Lys  Cys  Val  Leu
               20                   25                        30

Phe  Pro  Tyr  Gly  Gly  Cys  Gln  Gly  Asn  Gly  Asn  Lys  Phe  Tyr  Ser  Glu
               35                        40                   45

Lys  Glu  Cys  Arg  Glu  Tyr  Cys  Gly  Val  Pro  Gly  Asp  Gly  Asp  Glu  Glu
          50                    55                        60

Leu  Leu  Arg  Phe  Ser  Asn
 65                       70
```

( 2 ) INFORMATION FOR SEQ ID NO:26:

( i ) SEQUENCE CHARACTERISTICS:
        ( A ) LENGTH: 302 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: -
        ( B ) LOCATION: 1..302
        ( D ) OTHER INFORMATION: /label=polynucleotide
             / note= "j-x1-y-z(psti), insert in plasmid pM474,
             Figure 5"

( i x ) FEATURE:
        ( A ) NAME/KEY: sig_peptide
        ( B ) LOCATION: 27..89

( i x ) FEATURE:
        ( A ) NAME/KEY: mat_peptide
        ( B ) LOCATION: 90..293

( i x ) FEATURE:
        ( A ) NAME/KEY: CDS
        ( B ) LOCATION: 27..293

( x i ) SEQUENCE DESCRIPTION: SEQ ID NO:26:

```
AAGCTTAAAA  AAGGGTATAA  AATAAA  ATG  AAA  CAA  AGT  ACT  ATT  GCA  CTG  GCA          53
                                Met  Lys  Gln  Ser  Thr  Ile  Ala  Leu  Ala
```

|  |  |  |  |  |  | -21 |  | -20 |  |  |  |  |  | -15 |  |  |
|---|---|---|---|---|---|---|---|---|---|---|---|---|---|---|---|---|
| CTC | TTA | CCG | TTA | CTG | TTT | ACC | CCT | GTG | ACA | AAG | GCC | GCT | GTG | CTA | CCG | 101 |
| Leu | Leu | Pro | Leu | Leu | Phe | Thr | Pro | Val | Thr | Lys | Ala | Ala | Val | Leu | Pro | |
| | | -10 | | | | | -5 | | | | | | 1 | | | |
| CAA | GAA | GAA | GAA | GGC | TCG | GGA | ATG | GAC | TCC | CTA | GGT | CGC | GAG | GCC | AAA | 149 |
| Gln | Glu | Glu | Glu | Gly | Ser | Gly | Met | Asp | Ser | Leu | Gly | Arg | Glu | Ala | Lys | |
| 5 | | | | | 10 | | | | | 15 | | | | | 20 | |
| TGT | TAC | AAT | GAA | CTT | AAT | GGA | TGC | ACC | AAG | ATA | TAT | GAC | CCT | GTC | TGT | 197 |
| Cys | Tyr | Asn | Glu | Leu | Asn | Gly | Cys | Thr | Lys | Ile | Tyr | Asp | Pro | Val | Cys | |
| | | | | 25 | | | | | 30 | | | | | 35 | | |
| GGG | ACT | GAT | GGA | AAT | ACT | TAT | CCC | AAT | GAA | TGC | GTG | TTA | TGT | TTT | GAA | 245 |
| Gly | Thr | Asp | Gly | Asn | Thr | Tyr | Pro | Asn | Glu | Cys | Val | Leu | Cys | Phe | Glu | |
| | | | 40 | | | | | 45 | | | | | 50 | | | |
| AAT | CGG | AAA | CGC | CAG | ACA | TCG | ATC | CTC | ATT | CAA | AAA | TCT | GGG | CCT | TGC | 293 |
| Asn | Arg | Lys | Arg | Gln | Thr | Ser | Ile | Leu | Ile | Gln | Lys | Ser | Gly | Pro | Cys | |
| | | 55 | | | | | 60 | | | | | 65 | | | | |

TGAGGATCC 302

(2) INFORMATION FOR SEQ ID NO:27:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:27:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| -21 | -20 | | | | | -15 | | | | | -10 | | | | |
| Pro | Val | Thr | Lys | Ala | Ala | Val | Leu | Pro | Gln | Glu | Glu | Glu | Gly | Ser | Gly |
| -5 | | | | | 1 | | | | 5 | | | | | | 10 |
| Met | Asp | Ser | Leu | Gly | Arg | Glu | Ala | Lys | Cys | Tyr | Asn | Glu | Leu | Asn | Gly |
| | | | 15 | | | | | 20 | | | | | | 25 | |
| Cys | Thr | Lys | Ile | Tyr | Asp | Pro | Val | Cys | Gly | Thr | Asp | Gly | Asn | Thr | Tyr |
| | | 30 | | | | | 35 | | | | | 40 | | | |
| Pro | Asn | Glu | Cys | Val | Leu | Cys | Phe | Glu | Asn | Arg | Lys | Arg | Gln | Thr | Ser |
| | 45 | | | | | 50 | | | | | 55 | | | | |
| Ile | Leu | Ile | Gln | Lys | Ser | Gly | Pro | Cys | | | | | | | |
| 60 | | | | | 65 | | | | | | | | | | |

(2) INFORMATION FOR SEQ ID NO:28:

(i) SEQUENCE CHARACTERISTICS:
        (A) LENGTH: 343 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: -
        (B) LOCATION: 1..343
        (D) OTHER INFORMATION: /label=polynucleotide
        / note= "j-x1-y-z(AN68), insert in plasmid pM710,
        Figure 11"

(ix) FEATURE:
        (A) NAME/KEY: sig_peptide
        (B) LOCATION: 27..89

(ix) FEATURE:
        (A) NAME/KEY: mat_peptide
        (B) LOCATION: 90..329

( i x ) FEATURE:
   ( A ) NAME/KEY: CDS
   ( B ) LOCATION: 27..329

( x i ) SEQUENCE DESCRIPTION: SEQ ID NO:28:

| | | | | | | | | | | | | | | | | |
|---|---|---|---|---|---|---|---|---|---|---|---|---|---|---|---|---|
| AAGCTTAAAA | AAGGGTATAA | AATAAA | ATG | AAA | CAA | AGT | ACT | ATT | GCA | CTG | GCA | | | | | 53 |
| | | | Met | Lys | Gln | Ser | Thr | Ile | Ala | Leu | Ala | | | | | |
| | | | -21 | -20 | | | | -15 | | | | | | | | |
| CTC | TTA | CCG | TTA | CTG | TTT | ACC | CCT | GTG | ACA | AAG | GCC | GCT | GTG | CTA | CCG | 101 |
| Leu | Leu | Pro | Leu | Leu | Phe | Thr | Pro | Val | Thr | Lys | Ala | Ala | Val | Leu | Pro | |
| | | -10 | | | | | -5 | | | | | 1 | | | | |
| CAA | GAA | GAA | GAA | GGC | TCG | GGT | ATG | GCC | GCC | TGT | AAT | CTA | CCA | ATA | GTC | 149 |
| Gln | Glu | Glu | Glu | Gly | Ser | Gly | Met | Ala | Ala | Cys | Asn | Leu | Pro | Ile | Val | |
| 5 | | | | | 10 | | | | | 15 | | | | | 20 | |
| CGG | GGC | CCC | TGC | CGA | GCC | TTC | ATC | CAG | CTC | TGG | GCA | TTT | GAT | GCT | GTC | 197 |
| Arg | Gly | Pro | Cys | Arg | Ala | Phe | Ile | Gln | Leu | Trp | Ala | Phe | Asp | Ala | Val | |
| | | | | 25 | | | | | 30 | | | | | 35 | | |
| AAG | GGG | AAG | TGC | GTC | CTC | TTC | CCC | TAC | GGG | GGC | TGC | CAG | GGC | AAC | GGG | 245 |
| Lys | Gly | Lys | Cys | Val | Leu | Phe | Pro | Tyr | Gly | Gly | Cys | Gln | Gly | Asn | Gly | |
| | | | 40 | | | | | 45 | | | | | 50 | | | |
| AAC | AAG | TTC | TAC | TCA | GAG | AAG | GAG | TGC | AGA | GAG | TAC | TGC | GGT | GTC | CCT | 293 |
| Asn | Lys | Phe | Tyr | Ser | Glu | Lys | Glu | Cys | Arg | Glu | Tyr | Cys | Gly | Val | Pro | |
| | | 55 | | | | | 60 | | | | | 65 | | | | |
| GGT | GAT | GGT | GAT | GAG | GAG | CTG | CTG | CGC | TTC | TCC | AAC | TGACAACTGG | | | | 339 |
| Gly | Asp | Gly | Asp | Glu | Glu | Leu | Leu | Arg | Phe | Ser | Asn | | | | | |
| | 70 | | | | | 75 | | | | | 80 | | | | | |
| ATCC | | | | | | | | | | | | | | | | 343 |

( 2 ) INFORMATION FOR SEQ ID NO:29:

( i ) SEQUENCE CHARACTERISTICS:
      ( A ) LENGTH: 101 amino acids
      ( B ) TYPE: amino acid
      ( D ) TOPOLOGY: linear ( i i ) MOLECULE TYPE: protein ( x i ) SEQUENCE DESCRIPTION: SEQ ID NO:29:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| -21 | -20 | | | | -15 | | | | | -10 | | | | | |

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| -5 | | | | 1 | | | | | 5 | | | | | 10 | |

| Met | Ala | Ala | Cys | Asn | Leu | Pro | Ile | Val | Arg | Gly | Pro | Cys | Arg | Ala | Phe |
|---|---|---|---|---|---|---|---|---|---|---|---|---|---|---|---|
| | | | 15 | | | | | 20 | | | | 25 | | | |

| Ile | Gln | Leu | Trp | Ala | Phe | Asp | Ala | Val | Lys | Gly | Lys | Cys | Val | Leu | Phe |
|---|---|---|---|---|---|---|---|---|---|---|---|---|---|---|---|
| | | 30 | | | | | 35 | | | | | 40 | | | |

| Pro | Tyr | Gly | Gly | Cys | Gln | Gly | Asn | Gly | Asn | Lys | Phe | Tyr | Ser | Glu | Lys |
|---|---|---|---|---|---|---|---|---|---|---|---|---|---|---|---|
| | 45 | | | | 50 | | | | | 55 | | | | | |

| Glu | Cys | Arg | Glu | Tyr | Cys | Gly | Val | Pro | Gly | Asp | Gly | Asp | Glu | Glu | Leu |
|---|---|---|---|---|---|---|---|---|---|---|---|---|---|---|---|
| 60 | | | | | 65 | | | | 70 | | | | | | 75 |

| Leu | Arg | Phe | Ser | Asn |
|---|---|---|---|---|
| | | | | 80 |

( 2 ) INFORMATION FOR SEQ ID NO:30:

( i ) SEQUENCE CHARACTERISTICS:
      ( A ) LENGTH: 343 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
  ( A ) NAME/KEY: -
  ( B ) LOCATION: 1..343
  ( D ) OTHER INFORMATION: /label=polynucleotide
    / note= "j-x1-y-z((Q19K/Y46D), insert in plasmid
    pM727, Figure 22"

( i x ) FEATURE:
  ( A ) NAME/KEY: sig_peptide
  ( B ) LOCATION: 27..89

( i x ) FEATURE:
  ( A ) NAME/KEY: mat_peptide
  ( B ) LOCATION: 90..329

( i x ) FEATURE:
  ( A ) NAME/KEY: CDS
  ( B ) LOCATION: 27..329

( x i ) SEQUENCE DESCRIPTION: SEQ ID NO:30:

```
AAGCTTAAAA AAGGGTATAA AATAAA ATG AAA CAA AGT ACT ATT GCA CTG GCA           53
                              Met Lys Gln Ser Thr Ile Ala Leu Ala
                              -21 -20                     -15

CTC TTA CCG TTA CTG TTT ACC CCT GTG ACA AAG GCC GCT GTG CTA CCG           101
Leu Leu Pro Leu Leu Phe Thr Pro Val Thr Lys Ala Ala Val Leu Pro
        -10                  -5                   1

CAA GAA GAA GAA GGC TCG GGT ATG GCC GCC TGT AAT CTA CCA ATA GTC           149
Gln Glu Glu Glu Gly Ser Gly Met Ala Ala Cys Asn Leu Pro Ile Val
 5                  10                  15                  20

CGG GGC CCC TGC CGA GCC TTC ATC AAG CTC TGG GCA TTT GAT GCT GTC           197
Arg Gly Pro Cys Arg Ala Phe Ile Lys Leu Trp Ala Phe Asp Ala Val
              25                  30                  35

AAG GGG AAG TGC GTC CTC TTC CCC TAC GGG GGC TGC CAG GGC AAC GGG           245
Lys Gly Lys Cys Val Leu Phe Pro Tyr Gly Gly Cys Gln Gly Asn Gly
             40                  45                  50

AAC AAG TTC GAC TCA GAG AAG GAG TGC AGA GAG TAC TGC GGT GTC CCT           293
Asn Lys Phe Asp Ser Glu Lys Glu Cys Arg Glu Tyr Cys Gly Val Pro
         55                  60                  65

GGT GAT GGT GAT GAG GAG CTG CTG CGC TTC TCC AAC TGACAACTGG              339
Gly Asp Gly Asp Glu Glu Leu Leu Arg Phe Ser Asn
     70                  75                  80

ATCC                                                                    343
```

( 2 ) INFORMATION FOR SEQ ID NO:31:

( i ) SEQUENCE CHARACTERISTICS:
    ( A ) LENGTH: 101 amino acids
    ( B ) TYPE: amino acid
    ( D ) TOPOLOGY: linear ( i i ) MOLECULE TYPE: protein ( x i ) SEQUENCE DESCRIPTION: SEQ ID NO:31:

```
Met Lys Gln Ser Thr Ile Ala Leu Ala Leu Leu Pro Leu Leu Phe Thr
-21 -20                     -15                 -10

Pro Val Thr Lys Ala Ala Val Leu Pro Gln Glu Glu Glu Gly Ser Gly
 -5                  1                  5                  10

Met Ala Ala Cys Asn Leu Pro Ile Val Arg Gly Pro Cys Arg Ala Phe
             15                  20                  25

Ile Lys Leu Trp Ala Phe Asp Ala Val Lys Gly Lys Cys Val Leu Phe
         30                  35                  40

Pro Tyr Gly Gly Cys Gln Gly Asn Gly Asn Lys Phe Asp Ser Glu Lys
         45                  50                  55

Glu Cys Arg Glu Tyr Cys Gly Val Pro Gly Asp Gly Asp Glu Glu Leu
 60                  65                  70                  75
```

(2) INFORMATION FOR SEQ ID NO:32:

(i) SEQUENCE CHARACTERISTICS:
        (A) LENGTH: 343 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: -
        (B) LOCATION: 1..343
        (D) OTHER INFORMATION: /label=polynucleotide
        / note= "j-x1-y-z(R11S/Q19K/Y46D), insert in
        plasmids pM594 and pM765, Figure 24"

(ix) FEATURE:
        (A) NAME/KEY: sig_peptide
        (B) LOCATION: 27..89

(ix) FEATURE:
        (A) NAME/KEY: mat_peptide
        (B) LOCATION: 90..329

(ix) FEATURE:
        (A) NAME/KEY: CDS
        (B) LOCATION: 27..329

(xi) SEQUENCE DESCRIPTION: SEQ ID NO:32:

```
AAGCTTAAAA AAGGGTATAA AATAAA ATG AAA CAA AGT ACT ATT GCA CTG GCA         53
                              Met Lys Gln Ser Thr Ile Ala Leu Ala
                              -21 -20                     -15

CTC TTA CCG TTA CTG TTT ACC CCT GTG ACA AAG GCC GCT GTG CTA CCG         101
Leu Leu Pro Leu Leu Phe Thr Pro Val Thr Lys Ala Ala Val Leu Pro
        -10                  -5                   1

CAA GAA GAA GAA GGC TCG GGT ATG GCC GCC TGT AAT CTA CCA ATA GTC         149
Gln Glu Glu Glu Gly Ser Gly Met Ala Ala Cys Asn Leu Pro Ile Val
 5               10                  15                      20

AGC GGC CCC TGC CGA GCC TTC ATC AAG CTC TGG GCA TTT GAT GCT GTC         197
Ser Gly Pro Cys Arg Ala Phe Ile Lys Leu Trp Ala Phe Asp Ala Val
                 25                  30                  35

AAG GGG AAG TGC GTC CTC TTC CCC TAC GGG GGC TGC CAG GGC AAC GGG         245
Lys Gly Lys Cys Val Leu Phe Pro Tyr Gly Gly Cys Gln Gly Asn Gly
             40                  45                  50

AAC AAG TTC GAC TCA GAG AAG GAG TGC AGA GAG TAC TGC GGT GTC CCT         293
Asn Lys Phe Asp Ser Glu Lys Glu Cys Arg Glu Tyr Cys Gly Val Pro
         55                  60                  65

GGT GAT GGT GAT GAG GAG CTG CTG CGC TTC TCC AAC TGACAACTGG             339
Gly Asp Gly Asp Glu Glu Leu Leu Arg Phe Ser Asn
 70                  75                  80

ATCC                                                                    343
```

(2) INFORMATION FOR SEQ ID NO:33:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO:33:

```
Met Lys Gln Ser Thr Ile Ala Leu Ala Leu Leu Pro Leu Leu Phe Thr
-21 -20                     -15                      -10
```

(preceding, continued from previous page:)

```
Leu Arg Phe Ser Asn
                 80
```

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| -5 | | | | 1 | | | | 5 | | | | | | | 10 |

| Met | Ala | Ala | Cys | Asn | Leu | Pro | Ile | Val | Ser | Gly | Pro | Cys | Arg | Ala | Phe |
|---|---|---|---|---|---|---|---|---|---|---|---|---|---|---|---|
| | | | 15 | | | | | 20 | | | | | 25 | | |

| Ile | Lys | Leu | Trp | Ala | Phe | Asp | Ala | Val | Lys | Gly | Lys | Cys | Val | Leu | Phe |
|---|---|---|---|---|---|---|---|---|---|---|---|---|---|---|---|
| | | | 30 | | | | 35 | | | | | 40 | | | |

| Pro | Tyr | Gly | Gly | Cys | Gln | Gly | Asn | Gly | Asn | Lys | Phe | Asp | Ser | Glu | Lys |
|---|---|---|---|---|---|---|---|---|---|---|---|---|---|---|---|
| | 45 | | | | | 50 | | | | | 55 | | | | |

| Glu | Cys | Arg | Glu | Tyr | Cys | Gly | Val | Pro | Gly | Asp | Gly | Asp | Glu | Glu | Leu |
|---|---|---|---|---|---|---|---|---|---|---|---|---|---|---|---|
| 60 | | | | | 65 | | | | | 70 | | | | | 75 |

| Leu | Arg | Phe | Ser | Asn |
|---|---|---|---|---|
| | | | | 80 |

( 2 ) INFORMATION FOR SEQ ID NO:34:

( i ) SEQUENCE CHARACTERISTICS:
        ( A ) LENGTH: 96 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: -
        ( B ) LOCATION: 1..96
        ( D ) OTHER INFORMATION: /label=oligonucleotide
            / note= "j-x1, insert in pM710"

( i x ) FEATURE:
        ( A ) NAME/KEY: CDS
        ( B ) LOCATION: 1..96

( x i ) SEQUENCE DESCRIPTION: SEQ ID NO:34:

| ATG | AAA | CAA | AGT | ACT | ATT | GCA | CTG | GCA | CTC | TTA | CCG | TTA | CTG | TTT | ACC | 48 |
|---|---|---|---|---|---|---|---|---|---|---|---|---|---|---|---|---|
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | CCG | CAA | GAA | GAA | GAA | GGC | TCG | GGT | 96 |
|---|---|---|---|---|---|---|---|---|---|---|---|---|---|---|---|---|
| Pro | Val | Thr | Lys | Ala | Ala | Val | Leu | Pro | Gln | Glu | Glu | Glu | Gly | Ser | Gly | |
| | | | 20 | | | | | 25 | | | | | 30 | | | |

( 2 ) INFORMATION FOR SEQ ID NO:35:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| | | | 20 | | | | | 25 | | | | | 30 | | |

( 2 ) INFORMATION FOR SEQ ID NO:36:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:

(A) NAME/KEY: -
(B) LOCATION: 1..132
(D) OTHER INFORMATION: /label=polynucleotide
/ note= "j-x2, insert in plasmid pM776"

(ix) FEATURE:
(A) NAME/KEY: CDS
(B) LOCATION: 1..141

(xi) SEQUENCE DESCRIPTION: SEQ ID NO:36:

| ATG | AAA | CAA | AGT | ACT | ATT | GCA | CTG | GCA | CTC | TTA | CCG | TTA | CTG | TTT | ACC | 48 |
| --- | --- | --- | --- | --- | --- | --- | --- | --- | --- | --- | --- | --- | --- | --- | --- | --- |
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | CCC | CAA | GAA | GAG | GAA | GGA | TCA | GGG | 96 |
| --- | --- | --- | --- | --- | --- | --- | --- | --- | --- | --- | --- | --- | --- | --- | --- | --- |
| Pro | Val | Thr | Lys | Ala | Ala | Val | Leu | Pro | Gln | Glu | Glu | Glu | Gly | Ser | Gly | |
| | | | 20 | | | | | 25 | | | | | 30 | | | |

| GGT | GGG | CAA | CTG | GTA | ACT | GAA | GTC | ACC | AAG | AAA | GAA | GAC | TCG | GGT | 141 |
| --- | --- | --- | --- | --- | --- | --- | --- | --- | --- | --- | --- | --- | --- | --- | --- |
| Gly | Gly | Gln | Leu | Val | Thr | Glu | Val | Thr | Lys | Lys | Glu | Asp | Ser | Gly | |
| | | 35 | | | | 40 | | | | | 45 | | | | |

(2) INFORMATION FOR SEQ ID NO:37:

(i) SEQUENCE CHARACTERISTICS:
(A) LENGTH: 47 amino acids
(B) TYPE: amino acid
(D) TOPOLOGY: linear (ii) MOLECULE TYPE: protein (xi) SEQUENCE DESCRIPTION: SEQ ID NO:37:

| Met | Lys | Gln | Ser | Thr | Ile | Ala | Leu | Ala | Leu | Leu | Pro | Leu | Leu | Phe | Thr |
| --- | --- | --- | --- | --- | --- | --- | --- | --- | --- | --- | --- | --- | --- | --- | --- |
| 1 | | | | 5 | | | | | 10 | | | | | 15 | |

| Pro | Val | Thr | Lys | Ala | Ala | Val | Leu | Pro | Gln | Glu | Glu | Glu | Gly | Ser | Gly |
| --- | --- | --- | --- | --- | --- | --- | --- | --- | --- | --- | --- | --- | --- | --- | --- |
| | | | 20 | | | | | 25 | | | | | 30 | | |

| Gly | Gly | Gln | Leu | Val | Thr | Glu | Val | Thr | Lys | Lys | Glu | Asp | Ser | Gly |
| --- | --- | --- | --- | --- | --- | --- | --- | --- | --- | --- | --- | --- | --- | --- |
| | | 35 | | | | 40 | | | | | 45 | | | |

(2) INFORMATION FOR SEQ ID NO:38:

(i) SEQUENCE CHARACTERISTICS:
(A) LENGTH: 96 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: -
(B) LOCATION: 1..96
(D) OTHER INFORMATION: /label=oligonucleotide
/ note= "j-x3, insert in plasmid pM777"

(ix) FEATURE:
(A) NAME/KEY: CDS
(B) LOCATION: 1..96

(xi) SEQUENCE DESCRIPTION: SEQ ID NO:38:

| ATG | AAA | CAA | AGT | ACT | ATT | GCA | CTG | GCA | CTC | TTA | CCG | TTA | CTG | TTT | ACC | 48 |
| --- | --- | --- | --- | --- | --- | --- | --- | --- | --- | --- | --- | --- | --- | --- | --- | --- |
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | GAT | CAA | GAA | GAA | GAA | GGC | TCG | GGT | 96 |
| --- | --- | --- | --- | --- | --- | --- | --- | --- | --- | --- | --- | --- | --- | --- | --- | --- |
| Pro | Val | Thr | Lys | Ala | Ala | Val | Leu | Asp | Gln | Glu | Glu | Glu | Gly | Ser | Gly | |
| | | | 20 | | | | | 25 | | | | | 30 | | | |

(2) INFORMATION FOR SEQ ID NO:39:

(i) SEQUENCE CHARACTERISTICS:
(A) LENGTH: 32 amino acids ( B ) TYPE: amino acid
( D ) TOPOLOGY: linear ( i i ) MOLECULE TYPE: protein ( x i ) SEQUENCE DESCRIPTION: SEQ ID NO:39:

Met Lys Gln Ser Thr Ile Ala Leu Ala Leu Leu Pro Leu Leu Phe Thr
1               5                   10                  15

Pro Val Thr Lys Ala Ala Val Leu Asp Gln Glu Glu Glu Gly Ser Gly
                20                  25                  30

( 2 ) INFORMATION FOR SEQ ID NO:40:

( i ) SEQUENCE CHARACTERISTICS:
( A ) LENGTH: 96 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: -
( B ) LOCATION: 1..96
( D ) OTHER INFORMATION: /label=oligonucleotide
/ note= "j-x4, insert in pM778"

( i x ) FEATURE:
( A ) NAME/KEY: CDS
( B ) LOCATION: 1..96

( x i ) SEQUENCE DESCRIPTION: SEQ ID NO:40:

ATG AAA CAA AGT ACT ATT GCA CTG GCA CTC TTA CCG TTA CTG TTT ACC    48
Met Lys Gln Ser Thr Ile Ala Leu Ala Leu Leu Pro Leu Leu Phe Thr
1               5                   10                  15

CCT GTG ACA AAG GCC GCT GTG CTA CCG CAA GAA GAA GAA GGC GAT GGT    96
Pro Val Thr Lys Ala Ala Val Leu Pro Gln Glu Glu Glu Gly Asp Gly
                20                  25                  30

( 2 ) INFORMATION FOR SEQ ID NO:41:

( i ) SEQUENCE CHARACTERISTICS:
( A ) LENGTH: 32 amino acids
( B ) TYPE: amino acid
( D ) TOPOLOGY: linear ( i i ) MOLECULE TYPE: protein ( x i ) SEQUENCE DESCRIPTION: SEQ ID NO:41:

Met Lys Gln Ser Thr Ile Ala Leu Ala Leu Leu Pro Leu Leu Phe Thr
1               5                   10                  15

Pro Val Thr Lys Ala Ala Val Leu Pro Gln Glu Glu Glu Gly Asp Gly
                20                  25                  30

( 2 ) INFORMATION FOR SEQ ID NO:42:

( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: -
( B ) LOCATION: 1..99
( D ) OTHER INFORMATION: /label=oligonucleotide
/ note= "j-x5, insert in plasmid pM779"

( i x ) FEATURE:

( A ) NAME/KEY: CDS
( B ) LOCATION: 1..99

( x i ) SEQUENCE DESCRIPTION: SEQ ID NO:42:

| ATG | AAA | CAA | AGT | ACT | ATT | GCA | CTG | GCA | CTC | TTA | CCG | TTA | CTG | TTT | ACC | 48 |
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | CCG | CAA | GAA | GAA | GAA | GGC | TCG | GGT | 96 |
| Pro | Val | Thr | Lys | Ala | Ala | Val | Leu | Pro | Gln | Glu | Glu | Glu | Gly | Ser | Gly | |
| | | | 20 | | | | | 25 | | | | | 30 | | | |

GAT                                                                                                99
Asp ( 2 ) INFORMATION FOR SEQ ID NO:43:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:43:

| Met | Lys | Gln | Ser | Thr | Ile | Ala | Leu | Ala | Leu | Leu | Pro | Leu | Leu | Phe | Thr |
| 1 | | | | 5 | | | | | 10 | | | | | 15 | |

| Pro | Val | Thr | Lys | Ala | Ala | Val | Leu | Pro | Gln | Glu | Glu | Glu | Gly | Ser | Gly |
| | | | 20 | | | | | 25 | | | | | 30 | | |

Asp ( 2 ) INFORMATION FOR SEQ ID NO:44:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: -
    ( B ) LOCATION: 1..102
    ( D ) OTHER INFORMATION: /label=polynucleotide
        / note= "j-x6, insert in plasmid 780"

( i x ) FEATURE:
    ( A ) NAME/KEY: CDS
    ( B ) LOCATION: 1..102

( x i ) SEQUENCE DESCRIPTION: SEQ ID NO:44:

| ATG | AAA | CAA | AGT | ACT | ATT | GCA | CTG | GCA | CTC | TTA | CCG | TTA | CTG | TTT | ACC | 48 |
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | CCG | CAA | GAA | GAA | GAA | GGC | TCG | GGT | 96 |
| Pro | Val | Thr | Lys | Ala | Ala | Val | Leu | Pro | Gln | Glu | Glu | Glu | Gly | Ser | Gly | |
| | | | 20 | | | | | 25 | | | | | 30 | | | |

GAT  GAT                                                                                           102
Asp  Asp ( 2 ) INFORMATION FOR SEQ ID NO:45:

( i ) SEQUENCE CHARACTERISTICS:
    ( A ) LENGTH: 34 amino acids
    ( B ) TYPE: amino acid
    ( D ) TOPOLOGY: linear ( i i ) MOLECULE TYPE: protein ( x i ) SEQUENCE DESCRIPTION: SEQ ID NO:45:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| | | | 20 | | | | | | 25 | | | | | 30 | |

Asp Asp ( 2 ) INFORMATION FOR SEQ ID NO:46:

( i ) SEQUENCE CHARACTERISTICS:
        ( A ) LENGTH: 105 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: -
        ( B ) LOCATION: 1..105
        ( D ) OTHER INFORMATION: /label=polynucleotide
            / note= "j-x7, insert in plasmid pM781"

( i x ) FEATURE:
        ( A ) NAME/KEY: CDS
        ( B ) LOCATION: 1..105

( x i ) SEQUENCE DESCRIPTION: SEQ ID NO:46:

| ATG | AAA | CAA | AGT | ACT | ATT | GCA | CTG | GCA | CTC | TTA | CCG | TTA | CTG | TTT | ACC | 48 |
|---|---|---|---|---|---|---|---|---|---|---|---|---|---|---|---|---|
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GTG | CTA | CCG | CAA | GAA | GAA | GAA | GGC | TCG | GGT | 96 |
|---|---|---|---|---|---|---|---|---|---|---|---|---|---|---|---|---|
| Pro | Val | Thr | Lys | Ala | Ala | Val | Leu | Pro | Gln | Glu | Glu | Glu | Gly | Ser | Gly | |
| | | | 20 | | | | | | 25 | | | | | 30 | | |

| GAT | GAT | GAT | | | | | | | | | | | | | | 105 |
|---|---|---|---|---|---|---|---|---|---|---|---|---|---|---|---|---|
| Asp | Asp | Asp | | | | | | | | | | | | | | |
| | | 35 | | | | | | | | | | | | | | |

( 2 ) INFORMATION FOR SEQ ID NO:47:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| | | | 20 | | | | | | 25 | | | | | 30 | |

| Asp | Asp | Asp |
|---|---|---|
| | | 35 |

( 2 ) INFORMATION FOR SEQ ID NO:48:

( i ) SEQUENCE CHARACTERISTICS:
        ( A ) LENGTH: 96 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: -
        ( B ) LOCATION: 1..96

( D ) OTHER INFORMATION: /label=oligonucleotide
/ note= "j-x8, insert in plasmid pM711"

( i x ) FEATURE:
( A ) NAME/KEY: CDS
( B ) LOCATION: 1..96

( x i ) SEQUENCE DESCRIPTION: SEQ ID NO:48:

| ATG | AAA | CAA | AGT | ACT | ATT | GCA | CTG | GCA | CTC | TTA | CCG | TTA | CTG | TTT | ACC | 48 |
|---|---|---|---|---|---|---|---|---|---|---|---|---|---|---|---|---|
| Met | Lys | Gln | Ser | Thr | Ile | Ala | Leu | Ala | Leu | Leu | Pro | Leu | Leu | Phe | Thr | |
| 1 | | | | 5 | | | | | 10 | | | | | 15 | | |

| CCT | GTG | ACA | AAG | GCC | GCT | GAC | GAC | CCG | CAA | GAA | GAA | GAA | GGC | TCG | GGT | 96 |
|---|---|---|---|---|---|---|---|---|---|---|---|---|---|---|---|---|
| Pro | Val | Thr | Lys | Ala | Ala | Asp | Asp | Pro | Gln | Glu | Glu | Glu | Gly | Ser | Gly | |
| | | | 20 | | | | | 25 | | | | | 30 | | | |

( 2 ) INFORMATION FOR SEQ ID NO:49:

( i ) SEQUENCE CHARACTERISTICS:
( A ) LENGTH: 32 amino acids
( B ) TYPE: amino acid
( D ) TOPOLOGY: linear ( i i ) MOLECULE TYPE: protein ( x i ) SEQUENCE DESCRIPTION: SEQ ID NO:49:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Ala | Asp | Asp | Pro | Gln | Glu | Glu | Glu | Gly | Ser | Gly |
|---|---|---|---|---|---|---|---|---|---|---|---|---|---|---|---|
| | | | 20 | | | | | 25 | | | | | 30 | | |

( 2 ) INFORMATION FOR SEQ ID NO:50:

( i ) SEQUENCE CHARACTERISTICS:
( A ) LENGTH: 125 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: -
( B ) LOCATION: 1..125
( D ) OTHER INFORMATION: /label=insert
/ note= "insert in pKK223M, see Figure 1"

( i x ) FEATURE:
( A ) NAME/KEY: misc_feature
( B ) LOCATION: 1..5
( D ) OTHER INFORMATION: /label=5'-overhang ( i x ) FEATURE:
( A ) NAME/KEY: misc_feature
( B ) LOCATION: complement (121..125)
( D ) OTHER INFORMATION: /label=3'-overhang ( x i ) SEQUENCE DESCRIPTION: SEQ ID NO:50:

AATTCAAAAA AGGGTATAAA ATAAAATGAA ACAAAGTACT ATTGCACTGG CACTCTTACC    60

GTTACTGTTT ACCCCTGTGA CAAAGGCCGC TGTGCTACCG CAAGAAGAAG AAGGCTCGGG    120

AAGCT    125

( 2 ) INFORMATION FOR SEQ ID NO:51:

( i ) SEQUENCE CHARACTERISTICS:
( A ) LENGTH: 138 base pairs
( B ) TYPE: nucleic acid
( C ) STRANDEDNESS: double
( D ) TOPOLOGY: linear ( i i ) MOLECULE TYPE: cDNA ( i x ) FEATURE:
    ( A ) NAME/KEY: -
    ( B ) LOCATION: 1..138
    ( D ) OTHER INFORMATION: /label=fragment
        / note= "upper strand of Figure 4"

( i x ) FEATURE:
    ( A ) NAME/KEY: misc_feature
    ( B ) LOCATION: 1..4
    ( D ) OTHER INFORMATION: /label=5'-overhang ( x i ) SEQUENCE DESCRIPTION: SEQ ID NO:51:

AGCTTAAAAA AGGGTATAAA ATAAATGAA ACAAAGTACT ATTGCACTGG CACTCTTACC            60

GTTACTGTTT ACCCCTGTGA CAAAGGCCGC TGTGCTACCG CAAGAAGAAG AAGGCTCGGG         120

AATGGACTCC CTAGGTCG                                                                                    138

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..21
        ( D ) OTHER INFORMATION: /label=primer
            / note= "Hind III primer, see Figure 7 and Figures
                11, 22, 24,"

( x i ) SEQUENCE DESCRIPTION: SEQ ID NO:52:

ACGCAAGTTC ACGTAAAAAG C                                                                           21

( 2 ) INFORMATION FOR SEQ ID NO:53:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..40
        ( D ) OTHER INFORMATION: /label=primer
            / note= "AN68 primer, see Figure 8"

( x i ) SEQUENCE DESCRIPTION: SEQ ID NO:53:

CTATTGGTAG ATTACAGGCC GCGGCCTTTG TCACAGGGGT                                         40

( 2 ) INFORMATION FOR SEQ ID NO:54:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..21
        ( D ) OTHER INFORMATION: /label=primer
            / note= "pBR Bam HI primer, see Figure 9 and
                Figures 11, 22, 24"

( x i ) SEQUENCE DESCRIPTION: SEQ ID NO:54:

ACGATGCGTT CCGGCGTAGA G                                                                                    21

( 2 ) INFORMATION FOR SEQ ID NO:55:

( i ) SEQUENCE CHARACTERISTICS:
      ( A ) LENGTH: 155 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: -
      ( B ) LOCATION: 1..155
      ( D ) OTHER INFORMATION: /label=fragment
            / note= "Upper strand of Figure 10"

( i x ) FEATURE:
      ( A ) NAME/KEY: misc_feature
      ( B ) LOCATION: 1..4
      ( D ) OTHER INFORMATION: /label=5'-overhang ( i x ) FEATURE:
      ( A ) NAME/KEY: misc_feature
      ( B ) LOCATION: 152..155
      ( D ) OTHER INFORMATION: /label=3'-overhang ( x i ) SEQUENCE DESCRIPTION: SEQ ID NO:55:

AGCTTAAAAA AGGGTATAAA ATAAATGAA ACAAAGTACT ATTGCACTGG CACTCTTACC             60

GTTACTGTTT ACCCCTGTGA CAAAGGCCGC TGTGCTACCG CAAGAAGAAG AAGGCTCGGG          120

TATGGCCGCC TGTAATCTAC CAATAGTCCG GGGCC                                                        155

( 2 ) INFORMATION FOR SEQ ID NO:56:

( i ) SEQUENCE CHARACTERISTICS:
      ( A ) LENGTH: 200 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: -
      ( B ) LOCATION: 1..200
      ( D ) OTHER INFORMATION: /label=fragment
            / note= "Upper strand of Figure 12"

( i x ) FEATURE:
      ( A ) NAME/KEY: misc_feature
      ( B ) LOCATION: 1..4
      ( D ) OTHER INFORMATION: /label=5'-overhang ( i x ) FEATURE:
      ( A ) NAME/KEY: misc_feature
      ( B ) LOCATION: 197..200
      ( D ) OTHER INFORMATION: /label=3'-overhang ( x i ) SEQUENCE DESCRIPTION: SEQ ID NO:56:

AGCTTAAAAA AGGGTATAAA ATAAATGAA ACAAAGTACT ATTGCACTGG CACTCTTACC             60

GTTACTGTTT ACCCCTGTGA CAAAGGCCGC TGTGCTACCC CAAGAAGAGG AAGGATCAGG          120

GGGTGGGCAA CTGGTAACTG AAGTCACCAA GAAAGAAGAC TCGGGTATGG CCGCCTGTAA         180

TCTACCAATA GTCCGGGGCC                                                                                     200

( 2 ) INFORMATION FOR SEQ ID NO:57:

( i ) SEQUENCE CHARACTERISTICS:
    ( A ) LENGTH: 155 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: -
    ( B ) LOCATION: 1..155
    ( D ) OTHER INFORMATION: /label=fragment
        / note= "Upper stand of Figure 13"

( i x ) FEATURE:
    ( A ) NAME/KEY: misc_feature
    ( B ) LOCATION: 1..4
    ( D ) OTHER INFORMATION: /label=5'-overhang ( i x ) FEATURE:
    ( A ) NAME/KEY: misc_feature
    ( B ) LOCATION: 152..155
    ( D ) OTHER INFORMATION: /label=3'-overhang ( x i ) SEQUENCE DESCRIPTION: SEQ ID NO:57:

| | | | | | | |
|---|---|---|---|---|---|---|
| AGCTTAAAAA | AGGGTATAAA | ATAAAATGAA | ACAAAGTACT | ATTGCACTGG | CACTCTTACC | 60 |
| GTTACTGTTT | ACCCCTGTGA | CAAAGGCCGC | TGTGCTAGAT | CAAGAAGAAG | AAGGCTCGGG | 120 |
| TATGGCCGCC | TGTAATCTAC | CAATAGTCCG | GGGCC | | | 155 |

( 2 ) INFORMATION FOR SEQ ID NO:58:

( i ) SEQUENCE CHARACTERISTICS:
    ( A ) LENGTH: 155 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: -
    ( B ) LOCATION: 1..155
    ( D ) OTHER INFORMATION: /label=fragment
        / note= "Upper strand of Figure 14"

( i x ) FEATURE:
    ( A ) NAME/KEY: misc_feature
    ( B ) LOCATION: 1..4
    ( D ) OTHER INFORMATION: /label= 5- overhang ( i x ) FEATURE:
    ( A ) NAME/KEY: misc_feature
    ( B ) LOCATION: 152..155
    ( D ) OTHER INFORMATION: /label=3'-overhang ( x i ) SEQUENCE DESCRIPTION: SEQ ID NO:58:

| | | | | | | |
|---|---|---|---|---|---|---|
| AGCTTAAAAA | AGGGTATAAA | ATAAAATGAA | ACAAAGTACT | ATTGCACTGG | CACTCTTACC | 60 |
| GTTACTGTTT | ACCCCTGTGA | CAAAGGCCGC | TGTGCTACCG | CAAGAAGAAG | AAGGCGATGG | 120 |
| TATGGCCGCC | TGTAATCTAC | CAATAGTCCG | GGGCC | | | 155 |

( 2 ) INFORMATION FOR SEQ ID NO:59:

( i ) SEQUENCE CHARACTERISTICS:
    ( A ) LENGTH: 158 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: -

(B) LOCATION: 1..158
(D) OTHER INFORMATION: /label=fragment
/ note= "Upper strand of Figure 15"

(ix) FEATURE:
(A) NAME/KEY: misc_feature
(B) LOCATION: 1..4
(D) OTHER INFORMATION: /label=5'-overhang (ix) FEATURE:
(A) NAME/KEY: misc_feature
(B) LOCATION: 155..158
(D) OTHER INFORMATION: /label=3'-overhang (xi) SEQUENCE DESCRIPTION: SEQ ID NO:59:

```
AGCTTAAAAA AGGGTATAAA ATAAAATGAA ACAAAGTACT ATTGCACTGG CACTCTTACC        60
GTTACTGTTT ACCCCTGTGA CAAAGGCCGC TGTGCTACCG CAAGAAGAAG AAGGCTCGGG       120
TGATATGGCC GCCTGTAATC TACCAATAGT CCGGGGCC                              158
```

(2) INFORMATION FOR SEQ ID NO:60:

(i) SEQUENCE CHARACTERISTICS:
(A) LENGTH: 161 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: -
(B) LOCATION: 1..161
(D) OTHER INFORMATION: /label=fragment
/ note= "Upper strand of Figure 16"

(ix) FEATURE:
(A) NAME/KEY: misc_feature
(B) LOCATION: 1..4
(D) OTHER INFORMATION: /label=5'-overhang (ix) FEATURE:
(A) NAME/KEY: misc_feature
(B) LOCATION: 158..161
(D) OTHER INFORMATION: /label=3'-overhang (xi) SEQUENCE DESCRIPTION: SEQ ID NO:60:

```
AGCTTAAAAA AGGGTATAAA ATAAAATGAA ACAAAGTACT ATTGCACTGG CACTCTTACC        60
GTTACTGTTT ACCCCTGTGA CAAAGGCCGC TGTGCTACCG CAAGAAGAAG AAGGCTCGGG       120
TGATGATATG GCCGCCTGTA ATCTACCAAT AGTCCGGGGC C                          161
```

(2) INFORMATION FOR SEQ ID NO:61:

(i) SEQUENCE CHARACTERISTICS:
(A) LENGTH: 164 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: -
(B) LOCATION: 1..164
(D) OTHER INFORMATION: /label=fragment
/ note= "Upper strand of Figure 17"

(ix) FEATURE:
(A) NAME/KEY: misc_feature
(B) LOCATION: 1..4
(D) OTHER INFORMATION: /label=5'-overhang (ix) FEATURE:

(A) NAME/KEY: misc_feature
(B) LOCATION: 160..164
(D) OTHER INFORMATION: /label=3'-overhang ( x i ) SEQUENCE DESCRIPTION: SEQ ID NO:61:

```
AGCTTAAAAA AGGGTATAAA ATAAATGAA ACAAAGTACT ATTGCACTGG CACTCTTACC      60
GTTACTGTTT ACCCCTGTGA CAAAGGCCGC TGTGCTACCG CAAGAAGAAG AAGGCTCGGG    120
TGATGATGAT ATGGCCGCCT GTAATCTACC AATAGTCCGG GGCC                     164
```

( 2 ) INFORMATION FOR SEQ ID NO:62:

( i ) SEQUENCE CHARACTERISTICS:
(A) LENGTH: 155 base pairs
(B) TYPE: nucleic acid
(C) STRANDEDNESS: double
(D) TOPOLOGY: linear ( i i ) MOLECULE TYPE: cDNA ( i x ) FEATURE:
(A) NAME/KEY: -
(B) LOCATION: 1..155
(D) OTHER INFORMATION: /label=fragment
    / note= "Upper strand of Figure 18"

( i x ) FEATURE:
(A) NAME/KEY: misc_feature
(B) LOCATION: 1..4
(D) OTHER INFORMATION: /label=5'-overhang ( i x ) FEATURE:
(A) NAME/KEY: misc_feature
(B) LOCATION: 152..155
(D) OTHER INFORMATION: /label=3'-overhang ( x i ) SEQUENCE DESCRIPTION: SEQ ID NO:62:

```
AGCTTAAAAA AGGGTATAAA ATAAATGAA ACAAAGTACT ATTGCACTGG CACTCTTACC      60
GTTACTGTTT ACCCCTGTGA CAAAGGCCGC TGACGACCCG CAAGAAGAAG AAGGCTCGGG    120
TATGGCCGCC TGTAATCTAC CAATAGTCCG GGGCC                               155
```

( 2 ) INFORMATION FOR SEQ ID NO:63:

( i ) SEQUENCE CHARACTERISTICS:
(A) LENGTH: 25 base pairs
(B) TYPE: nucleic acid
(C) STRANDEDNESS: single
(D) TOPOLOGY: linear ( i i ) MOLECULE TYPE: DNA ( i x ) FEATURE:
(A) NAME/KEY: -
(B) LOCATION: 1..25
(D) OTHER INFORMATION: /label=primer
    / note= "Y46D primer, see Figure 20 and Figures 22, 24"

( x i ) SEQUENCE DESCRIPTION: SEQ ID NO:63:

```
GGGAACAAGT TCGACTCAGA GAAGG                                           25
```

( 2 ) INFORMATION FOR SEQ ID NO:64:

( i ) SEQUENCE CHARACTERISTICS:
(A) LENGTH: 31 base pairs
(B) TYPE: nucleic acid
(C) STRANDEDNESS: single
(D) TOPOLOGY: linear ( i i ) MOLECULE TYPE: DNA

```
( i x ) FEATURE:
        ( A ) NAME/KEY: -
        ( B ) LOCATION: 1..30
        ( D ) OTHER INFORMATION: /label=primer
                / note= "Q19K primer, see Figure 21 and Figures 22,
                24"

( x i ) SEQUENCE DESCRIPTION: SEQ ID NO:64:

CAAATGCCCA  GAGCTTGATG  AAGGCTCGGC  A                                              3 1

( 2 ) INFORMATION FOR SEQ ID NO:65:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: -
                ( B ) LOCATION: 1..27
                ( D ) OTHER INFORMATION: /label=primer
                        / note= "R11S primer, see Figure 23 and Figure 24"

( x i ) SEQUENCE DESCRIPTION: SEQ ID NO:65:

TCGGCAGGGG  CCGCTGACTA  TTGGTAG                                                    2 7
```